United States Patent [19]

Benner

[11] Patent Number: 5,216,141
[45] Date of Patent: Jun. 1, 1993

[54] OLIGONUCLEOTIDE ANALOGS CONTAINING SULFUR LINKAGES

[76] Inventor: Steven A. Benner, Grossmannstrasse 16, #7, CH-8049 Zurich, Switzerland

[21] Appl. No.: 202,528

[22] Filed: Jun. 6, 1988

[51] Int. Cl.$^5$ .............. C07H 19/00; C07H 21/00; C07D 473/00; C07C 13/08
[52] U.S. Cl. .................. 536/27.13; 544/242; 544/264; 544/265; 544/267; 544/276; 536/27.21; 536/27.2; 536/28.4; 536/28.5; 536/28.53
[58] Field of Search .............. 536/23, 26, 27, 28, 536/29, 24; 544/242, 264, 265, 267, 276

[56] References Cited

U.S. PATENT DOCUMENTS

| | | | |
|---|---|---|---|
| 3,846,402 | 11/1974 | Eckstein et al. | 536/27 |
| 4,415,732 | 11/1983 | Caruthers et al. | 536/27 |
| 4,469,863 | 9/1984 | Ts'o et al. | 536/27 |
| 4,808,708 | 2/1989 | Yoshida et al. | 536/24 |
| 4,837,311 | 6/1989 | Tam et al. | 536/22 |

FOREIGN PATENT DOCUMENTS

2122197A 1/1984 United Kingdom .
2122198 1/1984 United Kingdom .

OTHER PUBLICATIONS

Kawai, S. H. 1988 Abstract No. 318 No. Amer. Meeting of the Amer. Chem. Soc.
Noronha-Blob et al. J. of Med. Chem. vol. 20, No. 3, 1977, pp. 356-359.
Seela et al. (1987) Nucleic Acids Research vol. 15, No. 7, pp. 3113-3129.
B. M. Trosst & D. P. Curran, "Chemoselective Oxidation of Sulfides to Sulfones", Tetrahedron Letters 22: 1287-1290 (1981).
Noronha-Blob et al., Journal of Medicinal Chemistry, vol. 20, pp. 356-359 (1977).
Mungall et al., Journal of Organic Chemistry, vol. 42, pp. 703-706 (1977).
DiMenna et al., Journal of Medicinal Chemistry, vol. 21, pp. 1073-1076 (1978).
Harnden et al., Tetrahedron Letters, vol. 26, pp. 4265-4268 (1985).
Pitha et al., Biochemistry, vol. 10, pp. 4595-4602 (1971).

*Primary Examiner*—John W. Rollins
*Assistant Examiner*—Gary L. Kunz
*Attorney, Agent, or Firm*—Wolf, Greenfield & Sacks

[57] ABSTRACT

Analogs of DNA containing sulfides, sulfoxides, and sulfones as linking groups between subunits capable of forming bonds with natural oligonucleotides are described. The analogs are lipophilic, stable to chemical degradation under a wide range of conditions and stable to enzymatic degradation in vivo.

3 Claims, 23 Drawing Sheets

FIG 2
Building Block | Synthesis described in: | Example of an oligonucleotide analog containing sulfur made from this building block that would bind to the natural oligonucleotide trimer 5'-GpApC
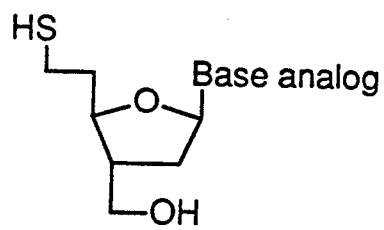
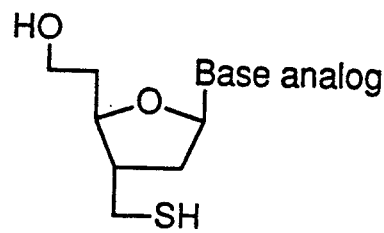
Example 1
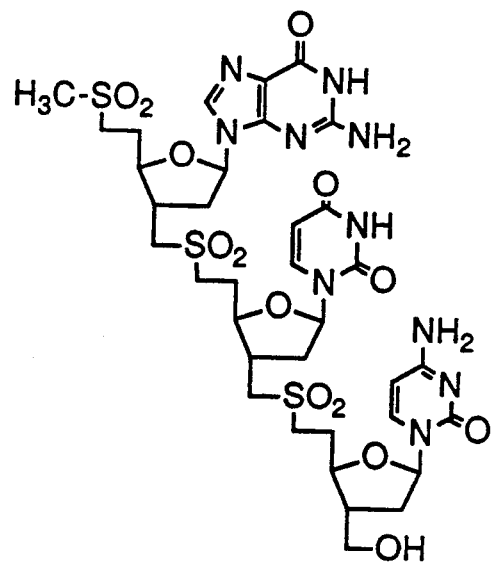
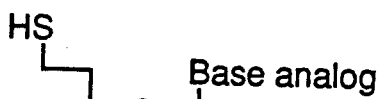
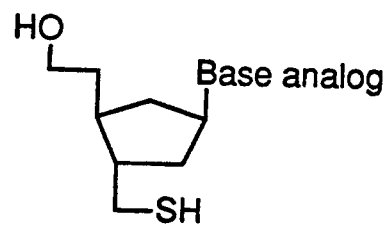
Example 2
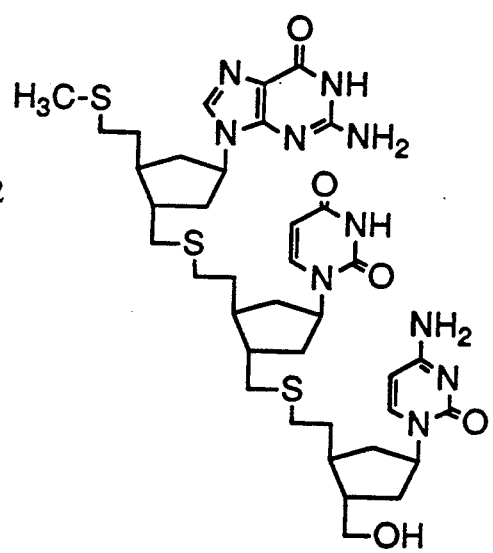

FIG 3
Flexible, with heteroatoms in chain:  Example of an oligonucleotide analog containing sulfur made from this building block that would bind to the natural oligonucleotide trimer 5'-GpApC
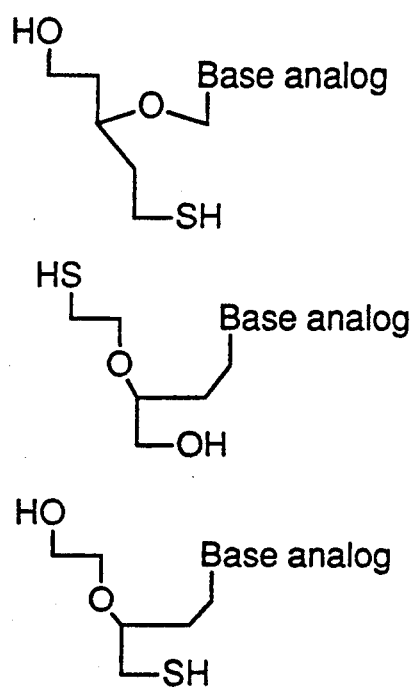
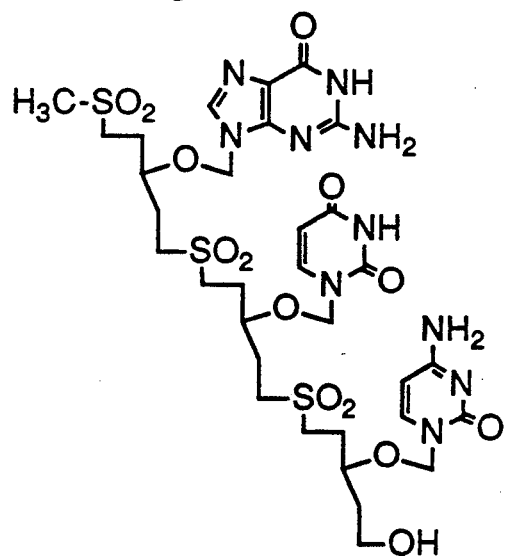
Flexible, without heteroatoms in chain
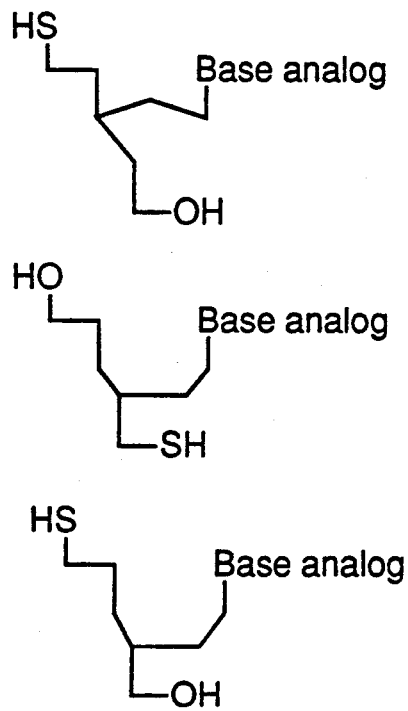
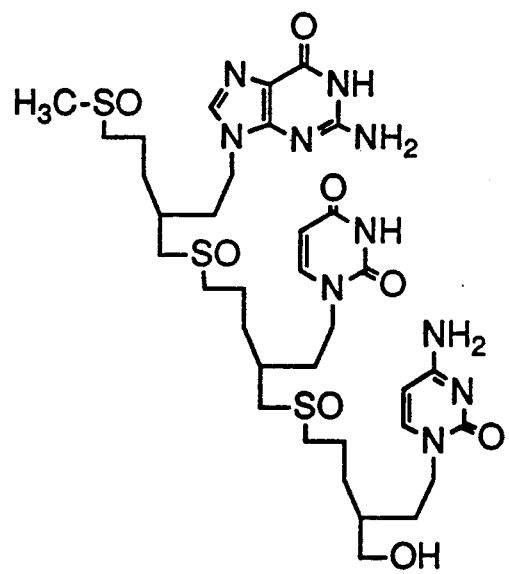

FIG 4a

| Class | Building Block | Skeleton from | Comments on source of precursor and synthesis |
|---|---|---|---|
| 0,1,1 | HOH$_2$C<br>H——Base analog<br>HSH$_2$C | Cystine | Commercial<br>Example 7 |
| 0,1,2 | HOH$_2$C<br>H——Base analog<br>H$_2$C<br>HSH$_2$C | Homocystine | Commercial<br>Example 8 |
| 0,1,3 | HOH$_2$C<br>H——Base Analog<br>H$_2$C<br>H$_2$C<br>CH$_2$SH | Glutamic acid | Commercial<br>See Figure 16 |
| 0,2,2 | CH$_2$OH<br>H$_2$C<br>H——Base analog<br>H$_2$C<br>CH$_2$SH | HO H<br>BnO⟋⟍OPv<br>40 | Intermediate in Example 5<br>See Figure 16 for more details |
| 1,1,0 | CH$_2$OH<br>⊢CH$_2$ Base analog<br>SH | p-Nitrophenyl-CO-OH$_2$C<br>⟋◁<br>O | Commercial<br>See Figure 16 |
| 1,1,1 | CH$_2$OH<br>⊢CH$_2$ Base analog<br>CH$_2$SH | CH$_2$OH<br>⊢CH$_2$·NH$_2$<br>CH$_2$SH | Mitsui Toatsu Chemicals Japanese patent JP 58,109,467<br>C.A. 99:175211r<br>Example 9 |
| 1,1,2 | CH$_2$OH<br>⊢CH$_2$ Base analog<br>CH$_2$<br>CH$_2$SH | CH$_2$OH<br>⊢CH$_2$OH<br>CH$_2$<br>CH$_2$SH | Harnden, M.R.<br>Jarvest, R. L.<br><u>Tetrahedron Lett.</u> 1985 <u>26</u> 4265-68.<br>Example 10 |

FIG 4b

| Class | Building Block | Skeleton from | Comments on source of precursor and synthesis |
|---|---|---|---|
| 1,2,0 | CH₂OH–CH₂–C(–CH₂-B¹)(SH)H | COOMe–CH₂–C(HO)(H)–CH₂NH₂ | Krogsgaard-Larsen, P.; Nielsen. L.; Falch, E.; Curtis, D. R.; *J. Med. Chem.* 1985 28 1612-17. See Figure 16 |
| 1,2,2 | CH₂OH–CH₂–C(H)(CH₂-B¹)–CH₂–CH₂SH | CH₂OH–CH₂–C(H)(CH₂-OH)–CH₂–CH₂SH | Wood, L.L.; Hartdegen, F. J.; Hahn, P. A. U.S. Patent 4,312,946 (Chem. Abstracts 97:19844c) |
| 1,3,0 | CH₂OH–CH₂–CH₂–C(H)(CH₂-B¹)(SH) | HOOC-(γ-butyrolactone) | Taniguchi, M.; Koga, K.; Yamada, S. *Tetrahedron*, 1974 30 3547 Figure 16 |
| 1,3º,1 | CH₂OH–CH₂–O–C(H)(CH₂-B¹)(CH₂SH) | p-Nitrophenyl-CO-OH₂C-(epoxide) | Commercial See Figure 16 |

FIG 4c

| Class | Building Block | Skeleton from | Comments on source of precursor and synthesis |
|---|---|---|---|
| 2,1,0 | H−C(CH$_2$OH)(SH)−CH$_2$-CH$_2$B$^1$ | HO−C(COOMe)(H)−C(H)(H)−CH$_2$NH$_2$ | Yoneta, Y.; Shibahara, S; Seki, S.; Fukatsu, S. U.S. Patent 4,290,972 Chem. Abstr. 96:7082u See Figure 16 |
| 2,1,1 | H−C(CH$_2$OH)(CH$_2$SH)−CH$_2$-CH$_2$B$^1$ | Structure 71 (benzyloxymethyl / tetrahydropyranyloxy intermediate with HO group) | Intermediate in Example 10 See Figure 16 |
| 2$^O$,1,1 | H−C(CH$_2$OH)(CH$_2$SH)−O−CH$_2$B$^1$ | H−C(CH$_2$OH)(CH$_2$SH)−OH | Commercial |
| 2$^O$,1,2 | H−C(CH$_2$OH)(CH$_2$-CH$_2$SH)−O−CH$_2$B$^1$ | H−C(CH$_2$OH)(CH$_2$-CH$_2$SH)−OH | From homocystine Commercial |
| 2,1,3$^O$ | H−C(CH$_2$OH)(O-CH$_2$-CH$_2$SH)−CH$_2$-CH$_2$B$^1$ | HO−C(COOMe)(H)−C(H)(H)−CH$_2$NH$_2$ | ISOSTERIC Yoneta, Y.; Shibahara, S; Seki, S.; Fukatsu, S. U.S. Patent 4,290,972 Chem. Abstr. 96:7082u See Figure 16 |

| Class | Building Block | Skeleton from | Comments on source of precursor and synthesis |
|---|---|---|---|
| 2,2,2 | $\begin{array}{c} CH_2OH \\ | \\ CH_2 \\ | \\ H-C-CH_2\cdot CH_2-B^1 \\ | \\ CH_2 \\ | \\ CH_2SH \end{array}$ | 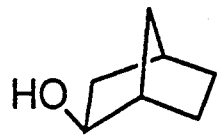 | ISOSTERIC See Example 11 |
| $2^O,2,2$ | $\begin{array}{c} CH_2OH \\ | \\ CH_2 \\ | \\ H-C-O-CH_2 B^1 \\ | \\ CH_2 \\ | \\ CH_2SH \end{array}$ | 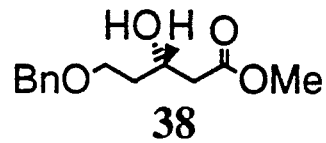 38 | ISOSTERIC See Example 5 |
| 2,3,1 | $\begin{array}{c} CH_2OH \\ | \\ CH_2 \\ | \\ CH_2 \\ | \\ H-C-CH_2\cdot CH_2-B^1 \\ | \\ CH_2SH \end{array}$ | 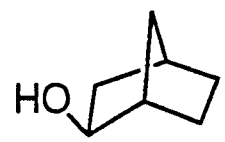 | ISOSTERIC See Example 11 |
| $3,1,3^O$ | $\begin{array}{c} CH_2OH \\ | \\ H-C-CH_2-CH_2CH_2-B^1 \\ | \\ O \\ | \\ CH_2 \\ | \\ CH_2SH \end{array}$ | $\begin{array}{c} COOH \\ | \\ H-C-OH \\ | \\ CH_2 \\ | \\ CH_2 \\ | \\ CH_2NH_2 \end{array}$ | Falch, E.; Hedegaard, A.; Nielsen, L.; Jensen, B. R.; Hjeds, H.; Krogsgaard-Larsen, P. J. Neurochem. 1986 47, 898-93 |

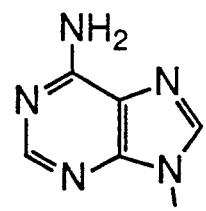 Adenine   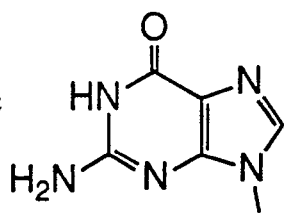 Guanine

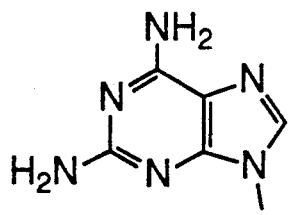 Diaminopurine

Shealy, Y.F.; O'Dell, C. A.; Arnett, G. J. Med. Chem. 1987 30 1090-94.

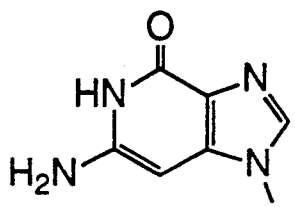 6-Amino-1,5-dihydroimidazo-[4,5-c]pyridin-4-one

Revankar, G. R.; Gupta. P.K.; Adams, A. D.; Dalley, N. K.; McKernan, P.A.; Cook, P.D.; Canonico, P.G.; Robins, R. K. J.Med.Chem. 1984 27 1389-96.

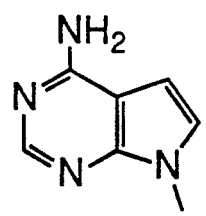 4-Aminopyrrolo-[2,3-d]pyrimidine (Tubercidin)

Kazimierczuk, Z.; Cottam, H. B.; Revankar, G. R.; Robins, R. K. J. Am. Chem. Soc. 1984 106 6379-82.

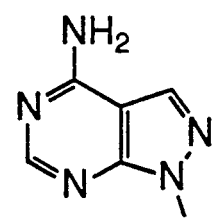 4-Aminopyrazolo-[3,4-d]pyrimidine

Kazimierczuk, Z.; Cottam, H. B.; Revankar, G. R.; Robins, R. K. J. Am. Chem. Soc. 1984 106 6379-82.

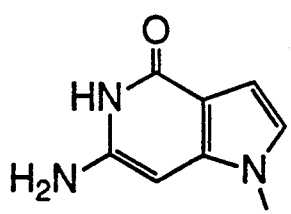 6-Amino-1H-pyrrolo-[3,2-c]-pyridin-4-one

Girgis, N. S.; Cottam, H.B.; Larson, S. B.; Robins, R. K.; Nucl. Acids Res. 1987 15 1217-26.

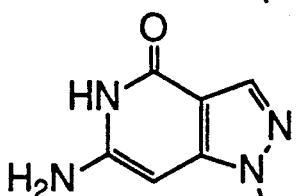 6-Amino-1H-pyrazolo-[4,3-c]pyridin-4-one

Ehler, K. W.; Robins, R.K.; Meyer, Jr., R. B. J. Med. Chem. 1977 20 317.

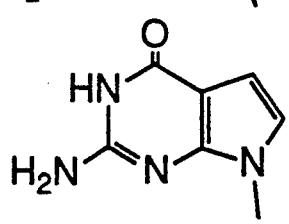 2-Amino-1H-pyrrolo-[2,3-d]pyrimidin-4-one

Ramasamy, K; Robins, R. K.; Revankar, G. R. Tetrahedron 1986 42 5869-5878.

FIG 5b

3,7-Dideaza-adenine

Ducrocq, C.; Bisagni, E.; Lhoste, J.-M.; Mispelter, J. Tetrahedron 1976 *32* 773-80.

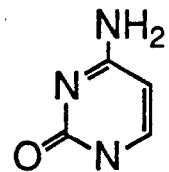

Cytosine

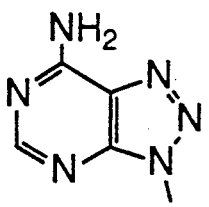

8-Azaadenine

Vince, R.; Daluge, S. J. Org. Chem 1980 *45* 531-33.

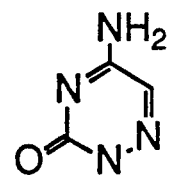

6-Azacytosine

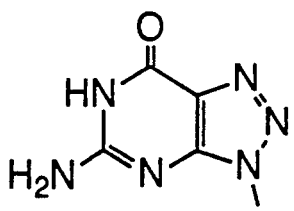

8-Azaguanine

Vince, R.; Turakhia, R. H.; Shannon, W. M.; Arnett, G. J. Med. Chem. 1987 *30* 2026.

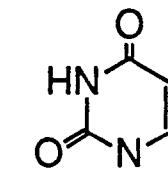

5-Iodouracil

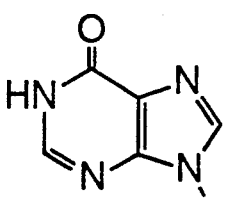

Hypoxanthine

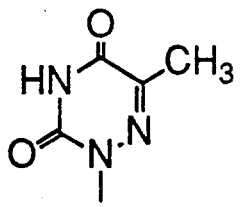

6-Azathymine

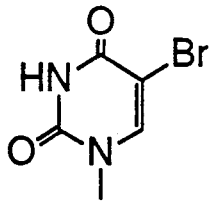

5-Bromouracil

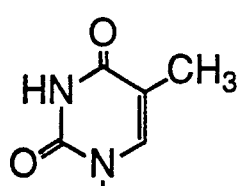

Thymine

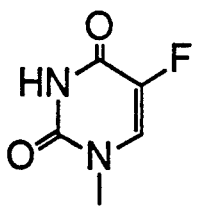

5-Fluorouracil

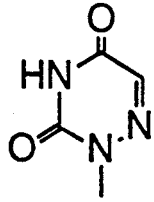

6-Azauracil

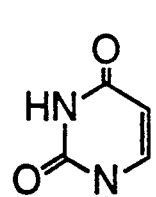

Uracil

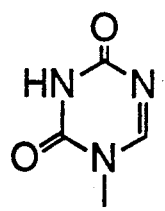

5-Azauracil

Glazer, R. I.; Knode, M. C.; Mol. Pharmacol. 1984 *26* 381.
Momparler, R. L.; Momparler, L. F.; Samson, J. Leuk. Res. 1984 *8* 1043.

pNp=p-nitrophenyl   MR=Mitsunobu Reaction

FIG 16b
(1,2,0)
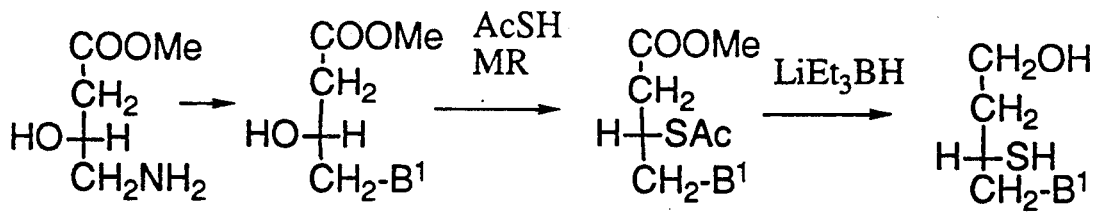
(1,3,0)
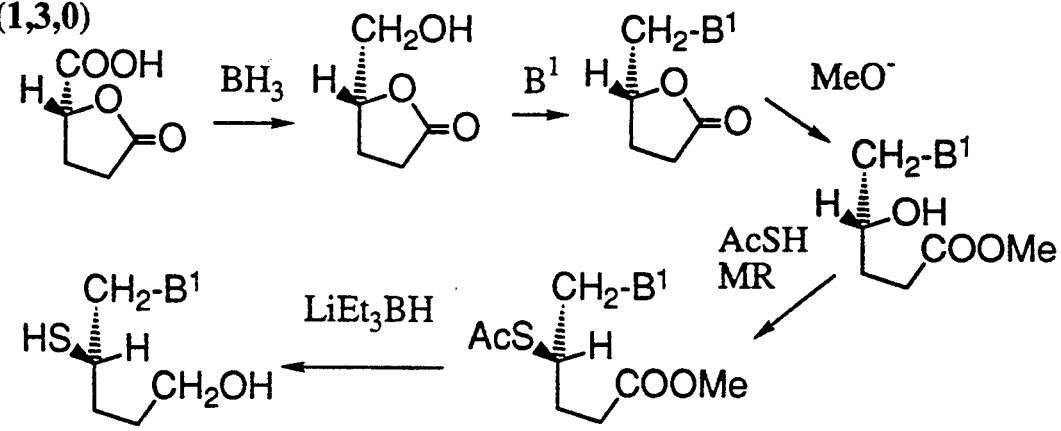
(1,3°,1)
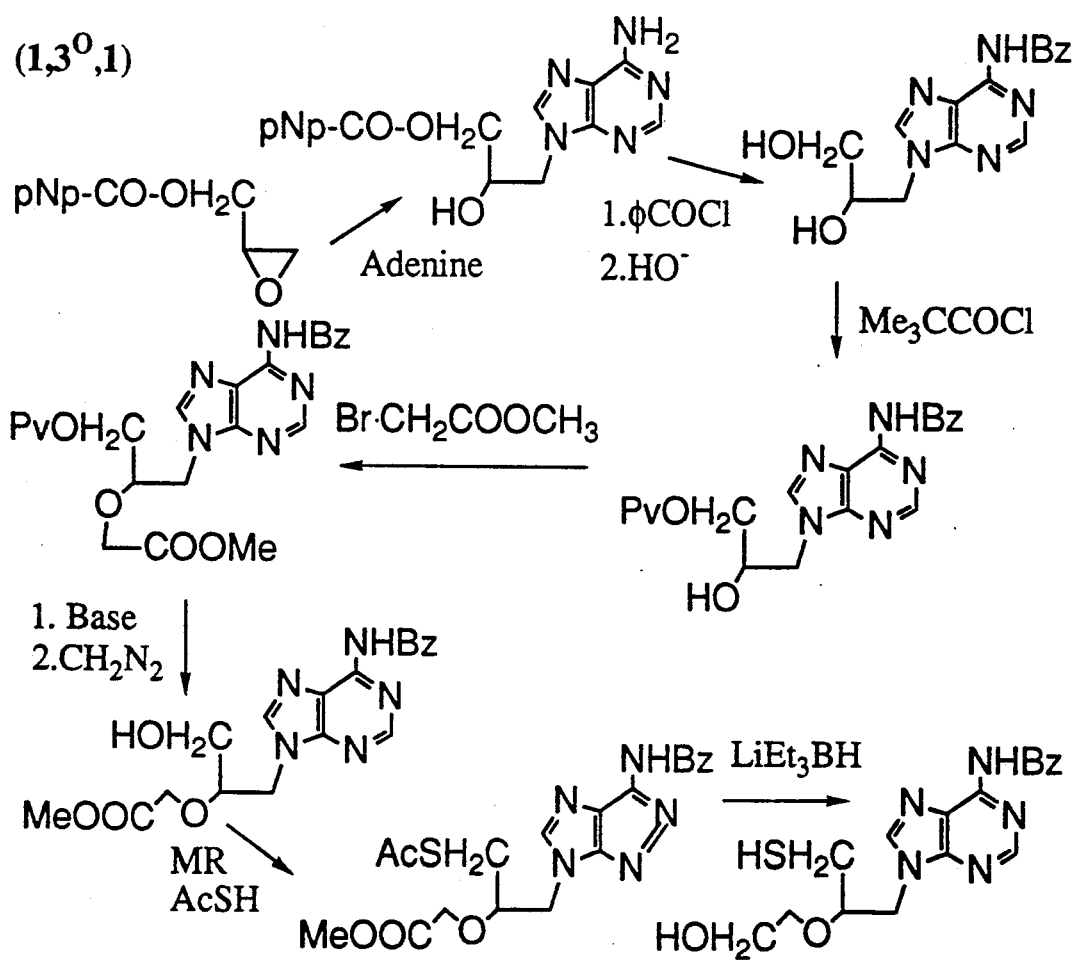

OLIGONUCLEOTIDE ANALOGS CONTAINING SULFUR LINKAGES

INTRODUCTION

Deoxyribonucleic acid (DNA) and ribonucleic acid (RNA) are molecules central to biological processes. As oligomers composed of five subunits (adenosine, A, cytidine, C, guanosine, G, uridine, U, and thymidine, T) joined by phosphodiester linkages, naturally occurring nucleic acids possess two notable structural properties.

First, oligonucleotides bind to complementary oligonucleotides (where "complementarity rules" are defined such that A in one oligonucleotide strand is paired against either U or T in the other, and G in one oligonucleotide strand is paired against C in the other, with the two strands anti-parallel) to form helical structures. The binding specificity is due to hydrogen bonds formed between bases on one oligonucleotide strand and complementary bases on the other. The thermodynamically stability of the helical structures is in part due to hydrophobic forces between bases stacked on top of each other in the double helical structure.

Second, information is coded in the oligonucleotide by the order of bases in the oligonucleotide strand. This information codes for proteins and nucleic acids necessary for the growth and replication of organisms. Oligonucleotides with defined sequence serve as genes, genetic regulatory agents, intracellular messages, especially for the synthesis of proteins, and possibly intercellular messages (Benner, S. A., *FEBS Lett.*, 1988, in press).

Many analogs of nucleosides and nucleotides have value as inhibitors of enzymes involved in the biosynthesis and metabolism of building blocks for DNA and RNA. However, analogs of oligonucleotides also have potential value, especially if they can bind sequence-specifically to natural oligonucleotides. For example, non-biodegradable oligonucleotide analogs that bind selectively to a natural oligonucleotide can serve as stable probes in vitro for complementary DNA. Molecules that bind selectively to a specific messenger RNA coding (mRNA) for a protein involved in cellular differentiation in Drosophila could serve as a tool for studying the control of development in Drosophila. Alternatively, a molecule binding selectively to a mRNA coding for a viral protein could inhibit the synthesis of this protein selectively, and therefore inhibit the growth of the virus, without inhibiting the biosynthesis of other proteins in the organism infected by the virus. Finally, a molecule that binds selectively to an intercellular nucleic acid involved in cell growth could inhibit the action of this nucleic acid, and thus modulate cell growth.

The "complementarity rules" mentioned above could, in principle, guide the design of a molecule that presents to a natural oligonucleotide an array of hydrogen bond donor and acceptor groups that would form the basis for a specific binding to this oligonucleotide. However, it is difficult to design a molecular skeleton with the desired molecular properties to hold this array.

For example, the complementary natural oligonucleotide is a readily designed molecule that will bind with sequence specificity to a target natural oligonucleotide. Indeed, oligonucleotides complementary to biologically active oligonucleotides are used as probes and, more recently have been found to inhibit the biological function of the target oligonucleotide, presumably because they form double helical structures specifically with their target oligonucleotide. "Anti-sense RNA", RNA complementary to messenger RNA coding for a specific protein, when microinjected into frog eggs, inhibits the expression of the coded proteins ("hybridization arrest"). "Anti-sense" DNA also is reported to inhibit the translation of complementary mRNA (Paterson, et al. *Proc. Nat. Acad. Sci.* 1977 74 4370-4374). Anti-sense nucleic acids inhibit the expression of viral genes in cells growing in tissue culture (Zamecnik, P. C.; Stephenson, M. L. *Proc. Nat. Acad. Sci.* 1978 75 280-284). "Hybridization arrest" of the translation of m-RNA by complementary oligonucleotides has been reported by many other authors, both in vivo (Kawasaki, E. S. *Nucl. Acids Res.* 1985 13 4991-5003) and in vitro (Minshull, J.; Hunt, T. *Nucl. Acids Res.* 1986 14 6433-6451) In several cases, natural oligonucleotides have been reported as being taken into cells in tissue culture and displaying antiviral effects. (Zamecnik, P. C.; Stephenson, M. L. 1978 *Proc. Nat. Acad. Sci.* 75 280-284. Stephenson, M. L.; Zamecnik, P. C. *Proc. Nat. Acad. Sci.* 1978 75 285-288. Zamecnik, P. C.; Goodchild, J.; Taguchi, Y.; Sarin, P. *Proc. Nat. Acad. Sci.* 1986 83 4143-4146).

However, natural oligonucleotides have two quite undesirable properties. First, they are rapidly degraded in biological environments due to the action of enzymes, particularly deoxyribonucleases (DNases), ribonucleases (RNases), and phosphodiesterases (Plesner, P.; Goodchild, J.; Kalckar, H. M.; Zamecnik, P. C. *Proc. Nat. Acad. Sci.* 1987 84 1936-1939).

Second, natural oligonucleotides do not easily penetrate biological barriers to reach their "target" oligonucleotide. Thus, one useful application of natural oligonucleotides as research tools requires that they be injected into cells with small needles, a delicate and tedious procedure.

In an attempt to circumvent these problems, several non-polar polymeric analogs of oligonucleotides containing subunits that lack the phosphate groups have been synthesized. Pitha and his coworkers have prepared a series of linear polymers of vinyl nucleides (Pitha, J.; Pitha, P. M.; Stuart, E. *Biochem.* 1971 4595-4602. Noronha-Blob, L.; Vengris, V. E.; Pitha, P. M.; Pitha, J. *J. Med. Chem.* 1977 20 356-359). As polymers, no control is possible in their synthetic scheme over the order of bases in the sequence. Therefore, although biological activity was observed in a variety of these compounds, it is impossible to determine whether these analogs can bind to specific sequences of natural oligonucleotides. Further, in the polymerization process, a new asymmetric center is created over which there is no synthetic control. Therefore, such polymers are complex mixtures of diastereomers.

Analogues of oligonucleotides where the phosphate bridging group is replaced by a carboxyl group have also been synthesized (Jones, A. S.; MacCoss, M.; Walker, R. T. *Biochem. Biophys. Acta* 1973 365 365-377). The analogs slowly hydrolyzed upon standing at neutral pH, and the polymer with adenosine formed an undefined complex with polyuridylic acid. Analogously, carbamate analogs of oligonucleotides have been synthesized (Mungall, W. S.; Kaiser, J. K. *J. Org. Chem.* 1977 42 703-706). Oligonucleotides have been constructed that contain 1,3 propanediol units between normal phosphate bases (Seela, F.; Kaiser, K. *Nucl. Acids Res.* 1987 15 3113-3129). These last molecules are not isosteric analogs of DNA, and cannot be prepared in the modified structural forms needed to modulate their binding affinity for natural oligonucleotides (vide infra). Finally, a recent abstract (Kawai, S. H.; Just, G.; Chin, J. *Abstracts,* North American Meeting of the American Chemical Society, #318, Jun. 8, 1988) has suggested that preliminary work may have begun on an oligonucleotide analog containing secondary hydroxyl groups and a bridging unit containing a thioether linkage. This structure again cannot be prepared in the modified structural forms needed to modulate their binding affinity for natural oligonucleotides (vide infra). Further, it appears that to form standard double helical structures with natural oligonucleotides, these molecules must adopt an unfavorable conformation where a polar hydroxyl group is adjacent to a nonpolar polymethylene unit. Recently, Miller, T'so, and their coworkers reported the synthesis of compounds that are isosteric analogs of DNA, differing only in that one oxygen of the phosphate group of each subunit is replaced by a methyl group. In all other structural aspects, these molecules are identical to naturally occurring oligonucleotides. These molecules, termed methylphosphonate DNA analogs, or methylphosphonates, lack phosphate-borne negative charges. A patent was recently awarded to the inventors of these molecules (U.S. Pat. No. 4,469,863, Sep. 4, 1984). Oligomethylphosphonates show several interesting biological properties. (For a review, see Miller, P. S.; Agris, C. H.; Aurelian, L.; Blake, K. R.; Murakami, A.; Reddy, M. P.; Spitz, S. A.; Ts'o, P.O.P. *Biochimie* 1985 67 769-776). They appear to cross cell membranes (Miller, P. S.; McParland, K. B.; Jayaraman, K.; Ts'o, P.O.P. *Biochem,* 1981 20 1874-1880) presumably because of their relative non-polarity when compared to natural oligonucleotides. One diastereomer of oligomethylphosphonate appear to form double helical structures with complementary natural oligonucleotides. Finally, these isomers appear to inhibit the biological action of mRNA coding for proteins, although activity is observed only at high concentrations (compared to those expected based on the proposed mechanism of action).

However, the methylphosphonates themselves have several undesirable chemical properties. First, substitution of a methyl group for an oxygen at phosphorus creates a chiral center. Therefore, oligomers composed of methylphosphonate building blocks are again complex mixtures of diastereomers. Further, apparently only one diastereomer of a methylphosphonate-linked dinucleotide can bind to a complementary natural oligonucleotide (Miller, P.S.; Yano, J.; Yano, E.; Carroll, C.; Jayaraman, K.; Ts'o, P.O.P. *Biochem.* 1979 18 5134–5143). The fact that oligomethylphosphonates are complex mixtures of diastereomers may be responsible in part for the low biological activity of these compounds (Murakami, A.; Blake, K. R.; Miller, P. S. *Biochem.* 1985 24 4041-4046).

Only dinucleotides of oligomethylphosphonates can at present be prepared diastereomerically pure (Miller, P. S.; Annan, N. D.; McParland, K. B.; Pulford, S. M. *Biochem.* 1982 21 2507-2512). Although considerable effort is being invested in efforts to improve methods for preparing methylphosphonates, (Marugg, J. E.; de Vroom, E.; Dreef, C. E.; van der Marel, G. A.; van Boom, J. H. *Nucl. Acids Res.* 1986 14 2171-2185; Lesnikowski, Z. J.; Wolakanin, P. J.; Stec, W. J. *Tetrahedron Lett.,* 1987 28 5535), there is at present no satisfactory synthetic method to control the chirality at phosphorus in longer oligomethylphosphonates, and their usefulness is limited for this reason.

A second problem arises from the chemical instability of methylphosphonate diesters. As with triesters of phosphoric acid, diesters of methylphosphonates are readily hydrolyzed in base. This problem is aggravated if the 5'-hydroxyl group of the oligonucleotide analog is unprotected. Under basic conditions, this hydroxyl group can attack the phosphonate linkage at the 3'-carbon atom via a kinetically favorable transition state with a six atom ring, causing the depolymerization of the oligophosphonate. Such reactions are known to occur with DNA analogs bearing phosphate triester groups, groups with chemical reactivity similar to methylphosphonates.

Basic conditions are required for the deprotection of bases in the reported procedure for the synthesis of oligomethylphosphonates. Complete deprotection of the bases is critical for full biological activity, as protecting groups block the functional groups that form the hydrogen bonds to complementary oligonucleotides. In the synthesis of natural oligonucleotides, complete deprotection is normally achieved by prolonged exposure of the protected oligonucleotide with base. Phosphodiester groups present in natural oligonucleotides are stable under these conditions. Methylphosphonate diesters are not. Thus, to avoid destroying oligomethylphosphonates, deprotection must be run under milder conditions for shorter times. Choice of these conditions necessarily represents a compromise. Deprotection cannot be complete without significant destruction of the methylphosphonate backbone, and significant hydrolysis of the backbone can only be avoided by accepting incomplete deprotection. Thus, it is perhaps not surprising that no satisfactory analytical data have yet been reported for the deprotected oligomethylphosphonates.

Finally, these analogs again are not apparently accessible in the modified structural forms needed to modulate their binding affinity for natural oligonucleotides (vide infra).

INVENTION

The object of this invention is to provide molecules, and building blocks for the synthesis of molecules, that can be designed to bind sequence specifically to target oligonucleotides ("oligonucleotide analogs") and that have the following properties:

(a) They should present an ordered array of groups capable of forming hydrogen bonds to a natural oligonucleotide, and thus be able to bind with a strong preference to a single oligonucleotide under the conditions of their application.

(b) Their affinity for natural oligonucleotides should be modulatable (i.e., strengtened or weakened) by incorporating into the oligonucleotide analog different subunits with different intrinsic binding abilities.

(c) They should be stable under a range of biological and chemical conditions, especially against enzymatic degradation in vivo and chemical degradation under the conditions of synthesis.

(d) They should not contain groups that bear a charge at neutral pH, and their overall polarity should be modulatable by varying the choice of building blocks.

The desirability of this combination of properties is neither obvious in the prior art, nor is it obvious what chemical structures would be likely to achieve them.

Nevertheless, molecules with such properties would have the maximum potential for practical application as research tools or in pharmaceutical chemistry.

BRIEF DESCRIPTION OF THE DRAWINGS

FIG. 2 depicts oxycyclic and carbocyclic rigid isoteric nucleoside analog building blocks and examples of oligonucleotide analogs containing sulfur that might be prepared from these.

FIG. 3 depicts flexible isosteric nucleoside analog building blocks and examples of oligonucleotide analogs containing sulfur that might be prepared from these.

FIG. 4a depicts flexible nucleoside analog building blocks and starting materials for their synthesis, where the number of atoms joining the base analog to the backbone is one or zero.

FIG. 4b depicts flexible nucleoside analog building blocks and starting materials for their synthesis, where the number of atoms joining the base analog to the backbone is 1 and the number of atoms separating the sulfurs in the oligonucleotide analog is from 3 to 5.

FIG. 4c depicts flexible nucleoside analog building blocks and starting materials for their synthesis, where the number of atoms joining the base analog to the backbone is 2 and the number of atoms separating the sulfurs in the oligonucleotide analog is from 2 to 5.

FIG. 4d depicts flexible nucleoside analog building blocks and starting materials for their synthesis, where the number of atoms joining the base analog to the backbone is 2 or 3, and the number of atoms separating the sulfurs in the oligonucleotide analog is 5.

FIG. 5a depicts base analogs that resemble purines and suitable for incorporation into oligonucleotide analogs joined by sulfide, sulfoxide, and sulfone linking groups.

FIG. 5b depicts base analogs that resemble purines and pyrimidines suitable for incorporation into oligonucleotide analogs joined by sulfide, sulfoxide, and sulfone linking groups.

FIG. 16b depicts a synthetic route for preparing flexible nucleoside analog building blocks where the number of atoms joining the base analog to the backbone is 1.

DESCRIPTION OF THE PREFERRED EMBODIMENTS

Figure 1:
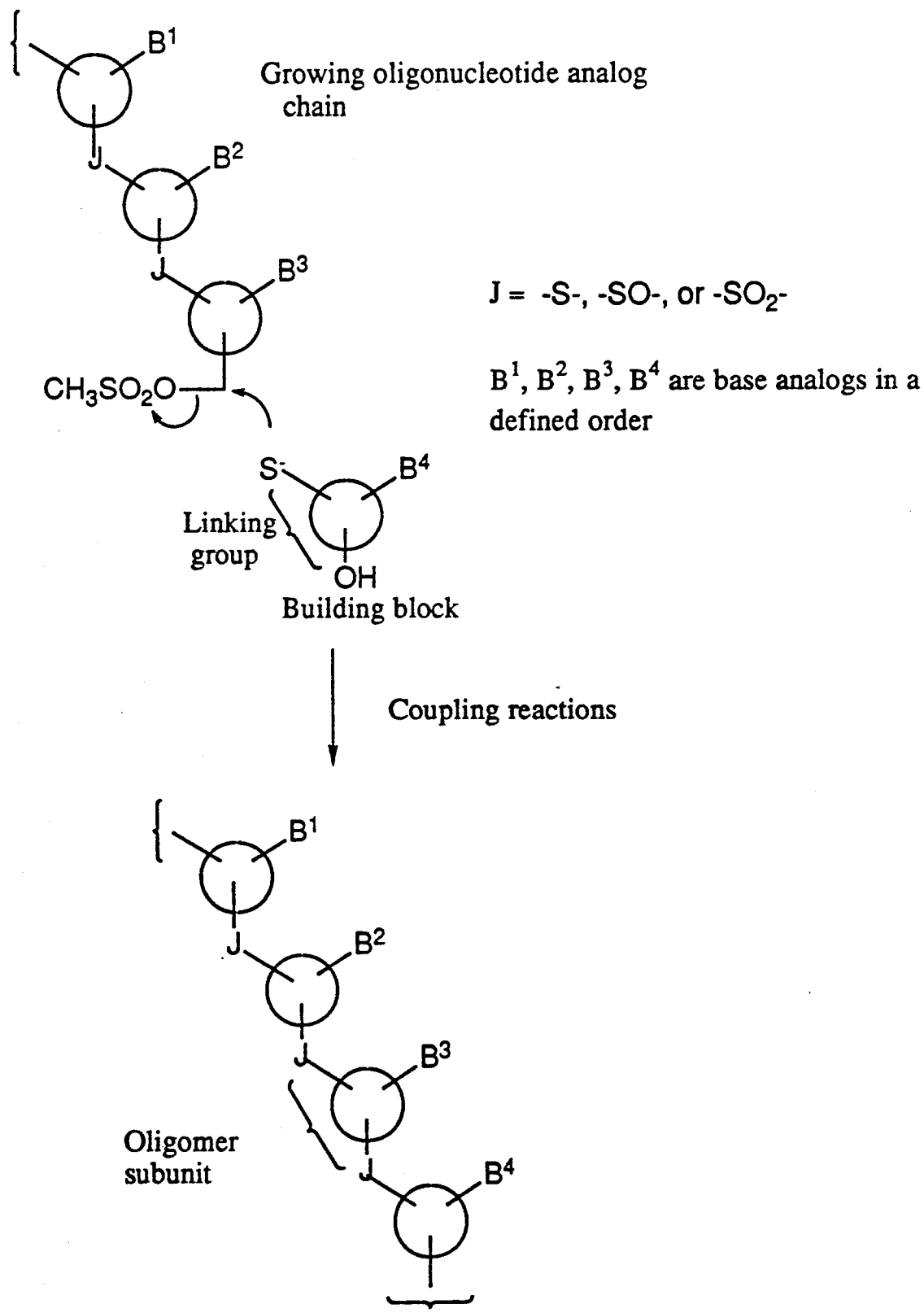
FIG. 1 depicts a general formula for oligonucleotide analogs joined by a sulfide, sulfoxide, and sulfone linking groups and a general reaction for preparing these.

Experiments in my laboratory with *Escherichia coli* showed that organic sulfides (compounds with the general formula RSR') sulfoxides (compounds with the general formula RSOR') and sulfones (compounds with the general formula $RSO_2R'$) all had biological effects consistent with the postulate that this structural unit (in contrast to a phosphate unit) was not an obstacle, and may in fact facilitate, the penetration of biological barriers. Further, certain sulfones (dimethyl sulfone and sulfolane in particular) were discovered to assist natural oligonucleotides in crossing cell membranes. Also, sulfides, sulfoxides, and sulfones proved to be stable to degradation, both chemical and biochemical. Finally, the sulfones were recognized as being achiral isosteric and isoelectronic analogs of phosphate diester anions.

Thus, the first oligonucleotide analogs invented substituted $CH_2—S—CH_2$, $CH_2—SO—CH_2$, and $CH_2—SO_2—CH_2$ groups for the $O—PO_2^-—O$ in natural oligonucleotides (FIG. 2). These oligonucleotide analogs are synthesized from building blocks disclosed in FIG. 2. Such building blocks are termed "isosteric," because they reproduce the shape and size of natural oligonucleotides, and "rigid," because they contain a ring. A less polar variant, also disclosed in FIG. 2, also replaces the ribose ring oxygen with a $—CH_2—$ group.

However, additional building blocks are necessary to permit the synthesis of oligonucleotide analogs to have the properties disclosed above. This lies in the need to control, or modulate, the binding affinity and polarity of oligonucleotide analogs assembled from these building blocks, as explained below.

An oligonucleotide analog presenting a specific array of hydrogen bond donor and acceptor groups will bind to any natural oligonucleotide that contains a sequence with a complementary array of hydrogen bond donor and acceptor groups. Thus, whether or not the analog binds to a unique natural oligonucleotide in a complex biological mixture containing many natural oligonucleotide depends on how many of the natural oligonucleotides present contain a subsequence that is complementary to the oligonucleotide analog and capable of forming a complex under the ambient conditions.

For example, mammalian genomes often contain approximately 10 billion bases. In a pool of oligonucleotides this large, sequences 16 bases in length occur once on the average. Shorter sequences occur more frequently. For example, an oligonucleotide sequence 10 bases in length is expected to be found (on average) some 4000 times in the genome. This means that an oligonucleotide analog composed of 10 subunits designed to serve as a probe for a gene containing a complementary sequence 10 bases long will not bind to a single oligonucleotide, but rather to approximately 4000 oligonucleotides in an extract from an organism with a genome this size at a permissive temperature. Should the oligonucleotide analog exert a biological effect in vivo as a result of its binding, this effect will not be specific for the target oligonucleotide, but rather will influence biological behavior in 4000 ways.

Naively, one might try to obtain higher specificity by making the oligonucleotide analog longer. However, with both natural oligonucleotides and certain of the analogs disclosed in FIG. 2, this would in fact not improve specificity. The melting temperature (the temperature at which two complementary oligonucleotides disassociate) of natural oligonucleotide helices 10 bases in length is above physiological temperature. Thus, although a longer oligonucleotide analog would bind more tightly to its target oligonucleotide at physiological temperature, it would also contain more subfragments capable of binding at physiological temperature to other oligonucleotides that contain complementary subsequences. Thus, at physiological temperature, the longer oligonucleotide analog would bind to many thousand natural oligonucleotides in addition to the target oligonucleotide. Should biological effects of binding be the focus of the application, the oligonucleotide analog would create many undesired biological effects.

Thus, certain of the oligonucleotide analogs disclosed in FIG. 2 (as well as certain of those disclosed in U.S. Pat. No. 4,469,863, and elsewhere in the literature, as described above) would bind to natural oligonucleotides too tightly to be able to be targeted specifically against a single oligonucleotide sequence under many conditions where such oligonucleotide analogs would have the most practical value.

The chemist must therefore be able to control, or modulate, the binding affinity of oligonucleotide analogs to the target oligonucleotide. In the example above, the binding interactions between each base pair should be weakened to the point where a 16-mer, but not a 15-mer, forms a stable helix with a complementary natural oligonucleotide at the defined temperature. One way to effect this modulation is by synthesizing an oligonucleotide analog from a pool of building blocks with different base analogs and linking skeletons with different intrinsic binding abilities to natural oligonucleotides. The ability of a subunit of an oligonucleotide analog to bind to a complementary base on a natural oligonucleotide depends in part on the structure of the base analog and linking group analog. The binding of the oligonucleotide analog as a whole is the sum of the binding interactions made by each subunit in the oligomer. Thus, the tightness of binding of the oligonucleotide analog to a complementary oligonucleotide can be modulated to the desired degree by incorporating a combination of weakly binding and strongly binding oligomer subunits.

Thus, a series of "flexible" oligonucleotide analog building blocks disclosed in FIGS. 3 and 4 were also invented. Flexible analogs do not contain a ring. An oligonucleotide analog incorporating such flexible subunits at one position will generally bind more weakly to a complementary oligonucleotide than an analogous oligonucleotide analog incorporating a rigid subunit at this position. Likewise, base analogs other than those occurring in natural oligonucleotides are in many cases capable of forming hydrogen bonds with complementary bases, but with different overall binding affinity. Oligonucleotide analogs incorporating base analogs forming more hydrogen bonds will form more stable complexes; for example, an oligonucleotide analog incorporating diaminopurine will bind more tightly to a natural oligonucleotide containing U than one incorporating adenine at the same position. Therefore, incorporating building blocks with different base analogs into an oligonucleotide analog therefore also permits the chemist to modulate the binding affinity of the analog for a natural oligonucleotide.

Flexible building blocks may be "isosteric" with natural occurring nucleosides, meaning that oligonucleotide analogs built from them contain the same number of atoms between base analogs as between bases in natural oligonucleotides (FIG. 3). However, in the flexible analogs, one atom is "missing" from the ribose ring. Isosteric subunits in oligonucleotide analogs are expected to fit best the standard double helical structures.

However, oligonucleotide analogs constructed from flexible analogs that are not isosteric can also bind to natural oligonucleotides. Representative examples of these non-isosteric building blocks are disclosed in FIG. 4. Incorporation of these into an oligonucleotide analog also serves to modulate the binding constant of the analog to a complementary oligonucleotide.

Further, the ability of an oligomer to pass across biological barriers (digestive system, blood vessel walls, cell membranes, for example) to reach a target oligonucleotide is influenced by the overall polarity of the oligomer, and perhaps by the degree to which it can be recognized by active transport systems. Further, membrane permeability and transport systems are different in bacteria, lower eukaryotes, and higher eukaryotes. Thus, subunits that contribute differently to the overall polarity of the oligonucleotide analog, and therefore differently to membrane and water solubility of the ligonucleotide analogs constructed from them, are valuable.

Building blocks therefore were invented to incorporate different numbers of carbon atoms and heteroatoms in the skeleton and base analog. Examples of these are disclosed in FIGS. 2, 3 and 4. Incorporation in an oligonucleotide analog of building blocks containing —$CH_2$— groups in place of heteroatoms allows the chemist to reduce the polarity of the oligonucleotide analog to achieve the optimal lipophilicity for a specific application.

A simple nomenclature for flexible building blocks is defined below. Building blocks that lack a ring are described by the general formula:

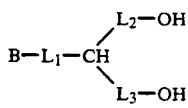

where B is a base analog capable of forming hydrogen bonds to a base on the target oligonucleotide, L is a linking group containing —CH$_2$— and —O— units with from 0 to 5 linking atoms (atoms in the connecting chain), C is an atom with defined chirality, L$_2$ and L$_3$ are linking groups containing —CH$_2$— and —O— units with from 0 to 6 linking atoms, with the sum of L$_2$ and L$_3$ less than or equal to 8, OH is a hydroxyl group, and SH is a thiol (or mercapto) group. Preferably, the number of linking atoms in L is less than or equal to the sum of the linking atoms in L$_2$ and L$_3$. This enables the oligonucleotide analogs to form a helix with a pitch that is compatible with the pitch preferred by natural oligonulceotide strands.

These skeletons are classified by three numbers designating the number of atoms in the chains that link atom C with the base, the —OH group, and the SH group respectively (i.e., the number of bonds between the C and the base, the OH group, and the SH group respectively, minus 1). Heteroatoms may be present in the linking groups, and this fact is designated by including the atomic symbol as a superscript. If heteroatoms are present, they are preferably oxygen. Illustrations of this nomenclature are shown in FIG. 4.

A similar classification scheme can be defined for skeletons containing a ring. Building blocks that contain a ring are described by the general formula:

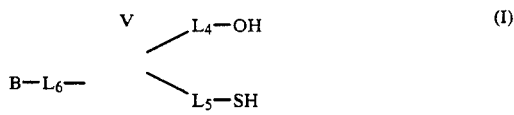

(I)

A computer literature search was performed by Dr. E. Zass to search for compounds with these general formulae. The only examples found which contained a CH$_2$—OH group, an —SH group, and a heterocycle unit containing either a 6 ring with at least 2 nitrogens, or a 6-5-ring system with at least 2 nitrogens are shown below. These compounds were the subject of British patent applications for compounds with antiviral activity (Eklind, K. I.; Gotthammar, K. B.; Hagbert, C. E.; Johansson, K. N. G.; Kovacs, Z. M. I.; Noren, J. O.; Stening, G. B. UK Pat. Appl. GB 2,122,198 *Chem. Abstr.* 1984 101 23900m. (Eriksson, B. F. H.; Gotthammar, K. B.; Johansson, K. N. G.; UK Pat. Appl. GB 2,122,197 *Chem. Abstr.* 1984 101 23899t).

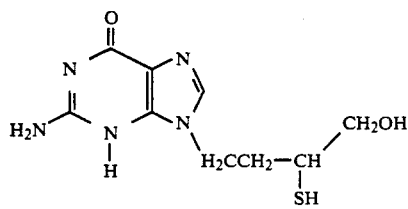

-continued

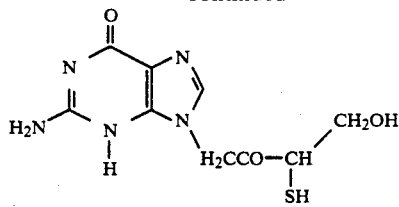

In both cases, the number of linking atoms in L (2) is greater than the sum of the linking atoms in X (1) and Y (0). Thus, although these molecules could in principle be used as building blocks to synthesize the oligonucleotide analogs disclosed here, oligonucleotide analogs made from these compounds would likely bind to natural nucleic acids only weakly if at all, due to the different pitch of the helix made by the two strands.

This patent teaches that a range of structurally analogous building blocks is necessary to construct non-ionic oligonucleotide analogs to have optimal applicability in a range of specific cases. While oligonucleotide analogs built from a single building block may have the combination of properties desired for a particular application under a specific set of conditions, this will be true only fortuitously. More generally, such an oligonucleotide analog will bind to a target oligonucleotide too tightly (or too loosely) in a particular environment at a particular temperature, or will have a membrane solubility too high (or a water solubility too high) for optimal permeation of a specific biological barrier under specific conditions.

Thus, we disclose here a series of compounds that can serve as building blocks for an oligonucleotide analog with properties that can be modulated to serve a particular function. For a specific application, the building blocks used as precursors for the oligonucleotide analog will depend on the desired application according to the following rules:

(a) The building blocks in the oligonucleotide analog are chosen based on the ability of their constituent base analogs to form hydrogen bonds with a complementary target oligonucleotide as would be predicted based on the assumption that the natural oligonucleotide and the oligonucleotide analog form double helical structures.

(b) The linker groups and base analogs in the building blocks are chosen to modulate the tightness of binding of the oligonucleotide analog to the target natural oligonucleotide, where the proportion of flexible subunits is greater for oligonucleotide analogs intended to bind to longer oligonucleotides at lower temperatures and greater ionic strength, than for oligonucleotide analogs intended to bind to shorter oligonucleotides at higher temperatures and lower ionic strength; and where the number of hydrogen bonds formed between strands is smaller for oligonucleotide analogs intended to bind to longer oligonucleotides at lower temperatures and greater ionic strength, than for oligonucleotide analogs intended to bind to shorter oligonucleotides at higher temperatures and lower ionic strength.

(c) The linker groups and base analogs in the building blocks are chosen to modulate the lipophilicity of the oligonucleotide analog, where increased number of —CH$_2$— groups replacing —O— groups, or —CH— groups replacing —N= groups, increases lipophilicity and decreases water solubility.

The preferred building blocks for constructing long (5-30 bases) oligonucleotide analogs for binding to complementary natural DNA and RNA are flexible. Referring to Formula 1, the sum of linking atoms (those in the chain) of linking group L is preferably from 0 and 5, and more preferably 0, 1 or 2; of X preferably between 1 and 5, and more preferably 1, 2, or 3; and of Y preferably between 0 and 5, and more preferably 2 or 3. Most preferably, the number of linking atoms in L, X, and Y is respectively 2, 2, and 2, or 2, 3, and 1, or 2, 1, and 3, or 0, 1, and 1. Further, the sum of the linking atoms in X and Y is preferably greater than or equal to the number of linking atoms in L.

The preferred building blocks for constructing short (1-10 bases) oligonucleotide analogs that bind tightly to complementary natural DNA and RNA are rigid. Preferably, the sum of linking atoms in groups K, M, and N (referring to Formula 2) is less than 4, more preferably 2; most preferably K is either a —CH$_2$ group or an oxygen, N is —CH$_2$—, M is a bond, and C, D, and E are CH groups. Preferably, the sum of the linking atoms in P and Q is less than 6, and Z contains less than 2 linking atoms; more preferably the sum of atoms in P and Q is 3, and Z is a bond, most preferably X is selected from the group consisting of —CH$_2$CH$_2$— and CH$_2$, and Y is selected from the group consisting of CH$_2$ and —CH$_2$CH$_2$—.

Figure 6A:
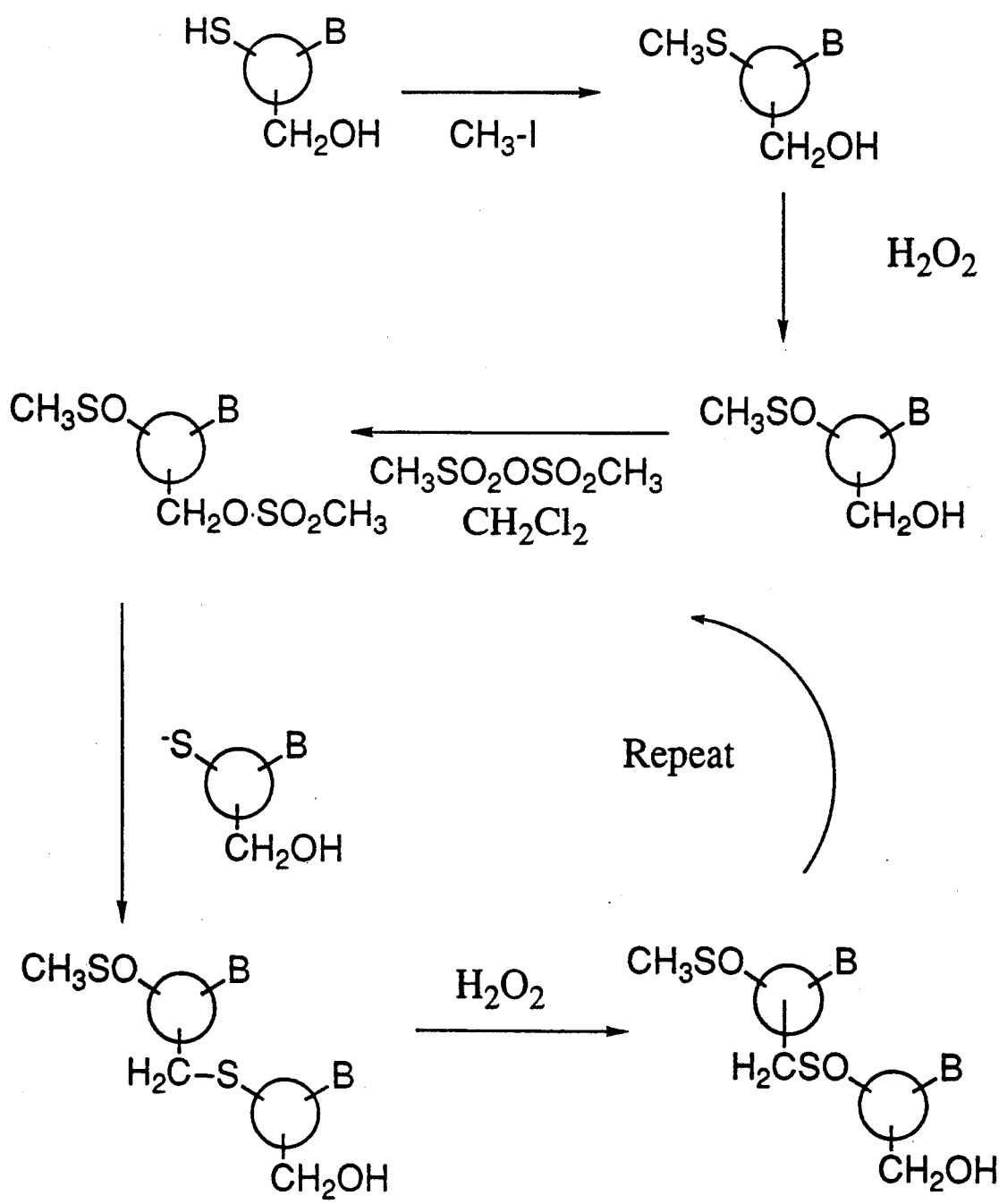
FIG. 6a depicts the reaction cycle for coupling building blocks to prepare oligonucleotide analogs joined by sulfide, sulfoxide, and sulfone linking groups.
Figure 6B:
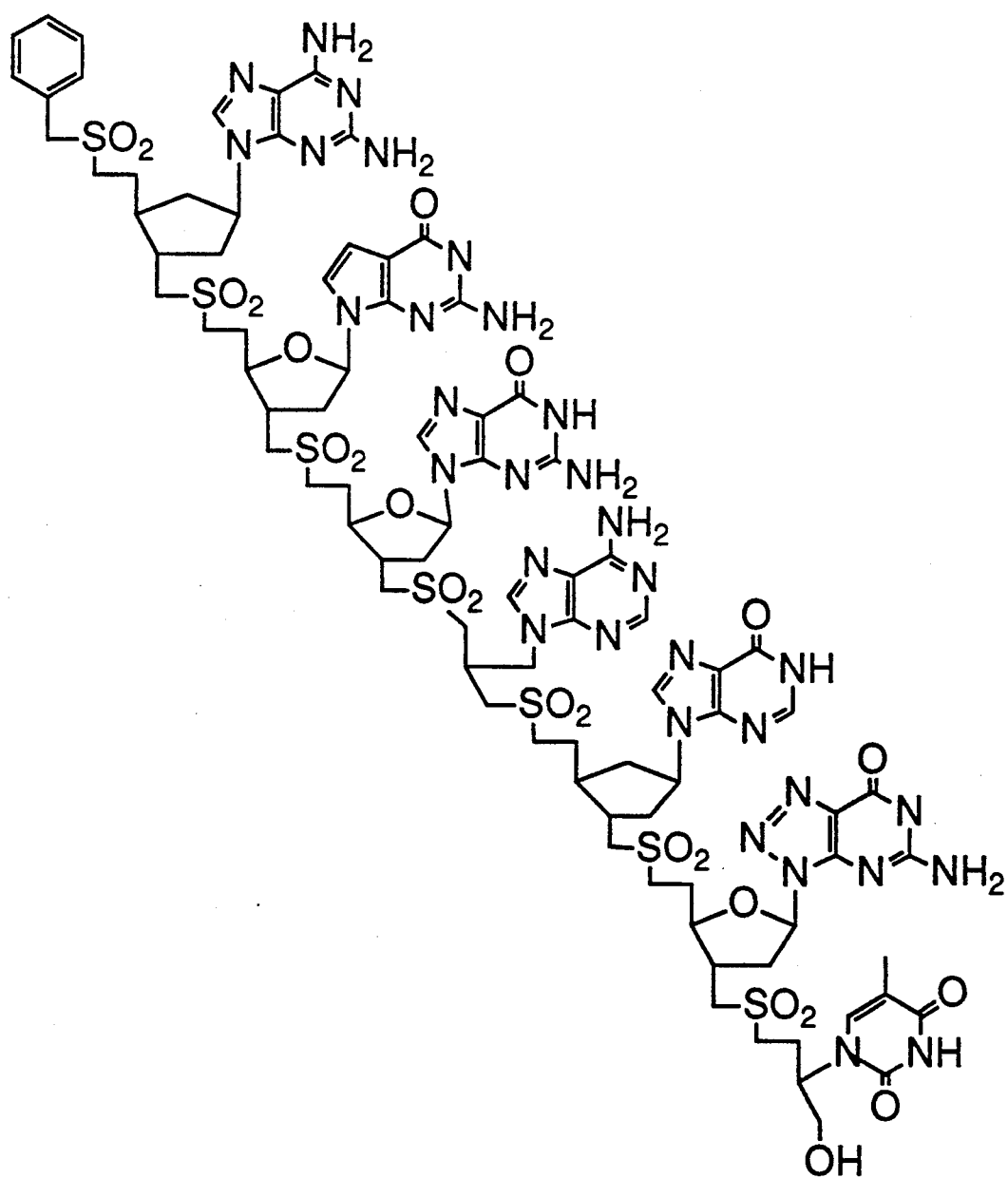
FIG. 6b depicts a structure of an exemplary oligonucleotide analog together with rationales for selecting individual constituent building blocks.

An example of an oligonucleotide analog composed with a selection of different linkers and bases using the rules disclosed above is shown in FIG. 6b.

Synthetic Methods

The building blocks for the synthesis of the oligonucleotide analogs themselves arise from three parts, a ring system that is the precursor for the base analogs, the functional groups (generally, —SH and —OH groups), and the skeleton that links the base analogs to the functional groups. In many of the compounds disclosed here, the syntheses of different skeletons is unique to the skeleton. However, a small number of synthetic methods are satisfactory for introducing base analogs and functional groups into most skeletons. Finally, a single preferred method is disclosed here for assembling building blocks to form an oligonucleotide analog.

The oligonucleotide analogs are built by sequential couplings of building blocks. The building blocks for the synthesis of the oligonucleotide analogs consist of four parts: (a) a linking moiety bearing (b) a single sulfhydryl group (—SH) (c) a single unprotected hydroxyl group (—OH, most preferably a primary alcohol group), and (d) a suitably protected base analog. An oligonucleotide analog with the desired sequence of building blocks is synthesized by stepwise condensation of the appropriate building blocks onto a growing oligonucleotide analog chain according to the scheme in FIG. 6. The sequence involves reaction of the free hydroxyl group of a growing oligomer chain with methanesulfonic acid anhydride, reaction of the resulting methanesulfonate with the thiolate anion of the next building block, and finally oxidation (if desired) of the resulting thioether to the sulfoxide or sulfone.

Depending on whether the desired product is (a) the sulfide, (b) the sulfoxide, or (c) the sulfone, the thioether is (a) not oxidized, (b) oxidized with 1 equivalent of aqueous hydrogen peroxide at 0° C., or (c) oxidized with potassium hydrogen persulfate (KHSO$_5$).

Protecting Groups

Standard protecting groups for amine groups in the bases must be used. Thus, the amine (NH$_2$) groups of adenine, cytosine, and guanine are preferably protected as their corresponding N-benzoyl or N-isobutyroyl amides. Amino groups on other base analogs are preferably protected as N-benzoyl amides.

Where the carbon skeleton permits the oxygen of uracil or thymidine (or a similar base analog) to form a 5 or 6 member ring via intramolecular attack of the heterocyclic ring oxygen on the activated methanesulfonate intermediate, the pyrimidine ring is preferably protected by an N-mesityl group (Welch, C. J.; Chattopadhyaya, J. B. *Acta Chem. Scand. B*, 1983, 37 147-150).

Chain Initiation

Building block (10 mmol) is dissolved in anhydrous dimethylformamide (5.2 g). Subsequent reactions are run under argon. To the solution is added a methanolic solution of benzyltrimethylammonium methoxide (11.0 mmol). The mixture is stirred at room temperature (5 min), and a solution of an end group containing a reactive leaving group (in this example, methyl iodide, 11 mmol) in DMF (5 ml) is added dropwise to yield the sulfide. The mixture is then stirred for 150 min to yield the first building block (intended for the oligonucleotide analog) with its thiol group blocked as a thioether. The nature of the blocking group is chosen to increase or decrease the lipophilicity of the final oligonucleotide analog, and may be attached to a solid support or a soluble polymer. However, it must be chosen so that it contains no unprotected functional groups that react under conditions of subsequent chain elongation.

Oxidation to Sulfoxide

The reaction mixture is cooled to 0° C., and a standardized solution of hydrogen peroxide (1.0 equivalents, 30% in water) is added. The mixture is then stirred allowed to warm slowly to room temperature over 30 minutes, and then stirred an additional 30 minutes at room temperature to yield the sulfoxide.

Oxidation to Sulfone

The reaction mixture is cooled to 0° C., and a suspension of potassium hydrogen persulfate (30 mmol, in 50 aqueous solution buffered with citrate to pH 5.0) is added. The mixture is then stirred at room temperature for 30 minutes to yield the sulfone. (Trost, B. M.; Curran, D. P. *Tetrahedron Lett.* 1981 22 1287-1290).

Chain extension: Mesylation

The product from the previous condensation (the growing oligonucleotide chain) (1 mmol) is dissolved in dry CH$_2$Cl$_2$ (50 ml) under an atmosphere of argon. To the stirred mixture is added slowly pyrrolidinopyridine (2.4 mmol) and methanesulfonic acid anhydride (2.3 mmol). The solvents are removed by evaporation, and the residue is dissolved in ether and filtered through Kieselgel. The methanesulfonate is then purified by high performance liquid chromatography.

Chain extension: S$_N$2 Reaction

A specimen of the desired building block (10 mmol) is dissolved in anhydrous dimethylformamide (5.2 g). To the solution is added a methanolic solution of benzyltrimethylammonium methoxide (11.0 mmol). The mixture is stirred at room temperature (5 min), and a solution of the methanesulfonate from the previous condensation step (11 mmol) in DMF (5 ml) is added dropwise. The reaction is stirred for 1 hour at room temperature, the solvents evaporated under vacuum (0.02 torr, 40° C.), the residue redissolved in methylene chloride, and the solution extracted with water. The organic phase is dried (magnesium sulfate), the solvents removed, and the product sulfide is then purified by high performance liquid chromatography. The cycle of reactions is then repeated, with building blocks added in the desired order in each cycle. Last, protecting groups are removed, preferably in aqueous $NH_4OH$.

Building Blocks

The synthesis of building blocks for the oligonucleotide analogs disclosed here is divided into two parts. The first involves obtaining the skeleton of carbon and heteroatoms that will become the linking unit. This skeleton contains a chiral center. The second involves the introduction of nucleoside base analogs and functional groups onto this skeleton to form the building blocks for the synthesis of the oligonucleotide analogs.

Introduction of the Thiol Group

Except in cases where the skeleton is derived from cystine, homocystine, or other molecules that already bear a thiol group and are readily obtained, the preferred method for introducing a thiol group is the Mitsunobu reaction, involving the conversion of a hydroxyl group to a $CH_3CO-S-$ group through the reaction of triphenylphosphine, diethylazodicarboxylate, and thioacetic acid. As the acetate derivative, the thiol group is protected against oxidation, yet can be deprotected by mild base or by reduction (e.g., with lithium triethylborohydride). For skeletons that can be obtained commercially already bearing a thiol group, this group is preferably protected as a dimeric disulfide, and the thiol is preferably generated by reduction prior to coupling.

Introduction of the Base Analog Ring System

Skeletons are obtained so that the carbon atom intended to bear the base analog is functionalized either with (a) an amino group, (b) a hydroxyl group, (c) a halogen group, (d) a $O-CH_2-L$ moiety, where L is a leaving group, (e) an epoxide, or (f) a ring system. Depending on the functional group involved and the nature of the ring system desired, one of six different methods is used to append the ring system:

(a) Where the skeleton already contains an amino group at the appropriate position, the ring system is built up by a series of condensation reactions, different for each base. The preferred method for constructing thymidine and uracil rings is by reaction with 2-methyl-3-ethoxyacryoyl isocyanate and 3-ethoxyacryoyl isocyanate respectively, followed by cyclization in dilute acid. (Farkas, J. "Synthesis of 5-methyl-2H-1,3-oxazine-2,4(3H)-dione" *Coll. Czech. Chem. Comm.* 1979 44 269-274) Adenine, guanine, and other purine rings can also be built up around an amino groups pre-existing in the skeleton.

(b) Where the skeleton contains a hydroxyl group at the appropriate position, the ring system is introduced by the Mitsunobu reaction of a corresponding base or base analog described below. This is the preferred method for introducing 6-chloropurine rings as precursors to adenine ring systems.

(c) Where the skeleton contains a halogen group at the appropriate position, the ring system is introduced by a nucleophilic substitution reaction with an appropriately protected heterocyclic ring or ring precursor. This is the preferred method for adding the 2-amino-6-chloropurine base analog to such skeletons.

(d) Where the skeleton bears a $O-CH_2-L$ moiety, where L is a leaving group, the ring system in introduced by reaction of an appropriately protected heterocyclic ring or ring precursor under electrophilic conditions. These protected heterocyclic rings or their precursors are already well known in the prior art. Thus, the preferred method for introducing a uracil, thymidine, adenine, guanine, and tubercidin, is by reaction of bistrimethylsilyloxypyrimidine, 2-trimethylsilyloxy-4-trimethylsilylaminopyrimidine, N-benzoyladenine, N-benzoylguanine, or N-benzoylaminopyrrolopyrimidine with a $O-CHR-Cl$ moiety on a skeleton.

(e) Where the skeleton bears an epoxide group, the preferred method for introducing a base is by nucleophilic substitution by a ring system at the less hindered site of the epoxide (DiMenna, W. D.; Piantadosi, C.; Lamb, R. G. *J. Med. Chem.* 1978, 21 1073-1076. Kondo, K.; Sato, T.; Takemoto, K. *Chem. Lett.* 1973, 967-968. Trost, B. M.; Kuo, G.-H.; Benneche, T. *J. Am. Chem. Soc.* 1988 110 621).

(f) Where the skeleton already bears a ring system, standard methods familiar to those skilled in the art enable the conversion of one ring system to another. Thus, one method for constructing cytidine rings is by conversion of uracil rings. The preferred method for constructing an adenine ring system from a 6-chloropurine ring system is reaction with methanolic ammonia. The preferred method for constructing a guanine ring system from a 2-amino-4-chloropurine ring system is hydrolysis in dilute aqueous acid.

Construction of the Carbon Skeleton

Precursors for the flexible skeletons shown in FIGS. 3 and 4 are shown in FIG. 4. Methods for constructing building blocks from a representative sample of these precursors are disclosed in the Examples using the general synthetic routes for introducing functional groups outlined above. These Examples teach one skilled in the art to construct appropriately functionalized flexible building blocks from the precursors shown in the Figures. Detailed procedures for constructing rigid skeleton (which involve more complicated synthetic transformations) are given in Examples 1 and 2.

Abbreviations

THF: tetrahydrofuran
EtOAc: ethyl acetate
RT: room temperature
NMR: nuclear magnetic resonance spectroscopy
GC: gas chromatography
IR: infrared spectrum
DEAD: diethylazodicarboxylate
THP: tetrahydropyranyl
Bz: benzoyl (Phenyl—CO—)

BDS: tert-butyldimethylsilyl
Bn: benzyl (Phenyl—CH$_2$)
Ac: acetyl (CH$_3$CO—)
Pv: pivaloyl (CH$_3$)$_3$CO—

EXAMPLES

Figure 7:
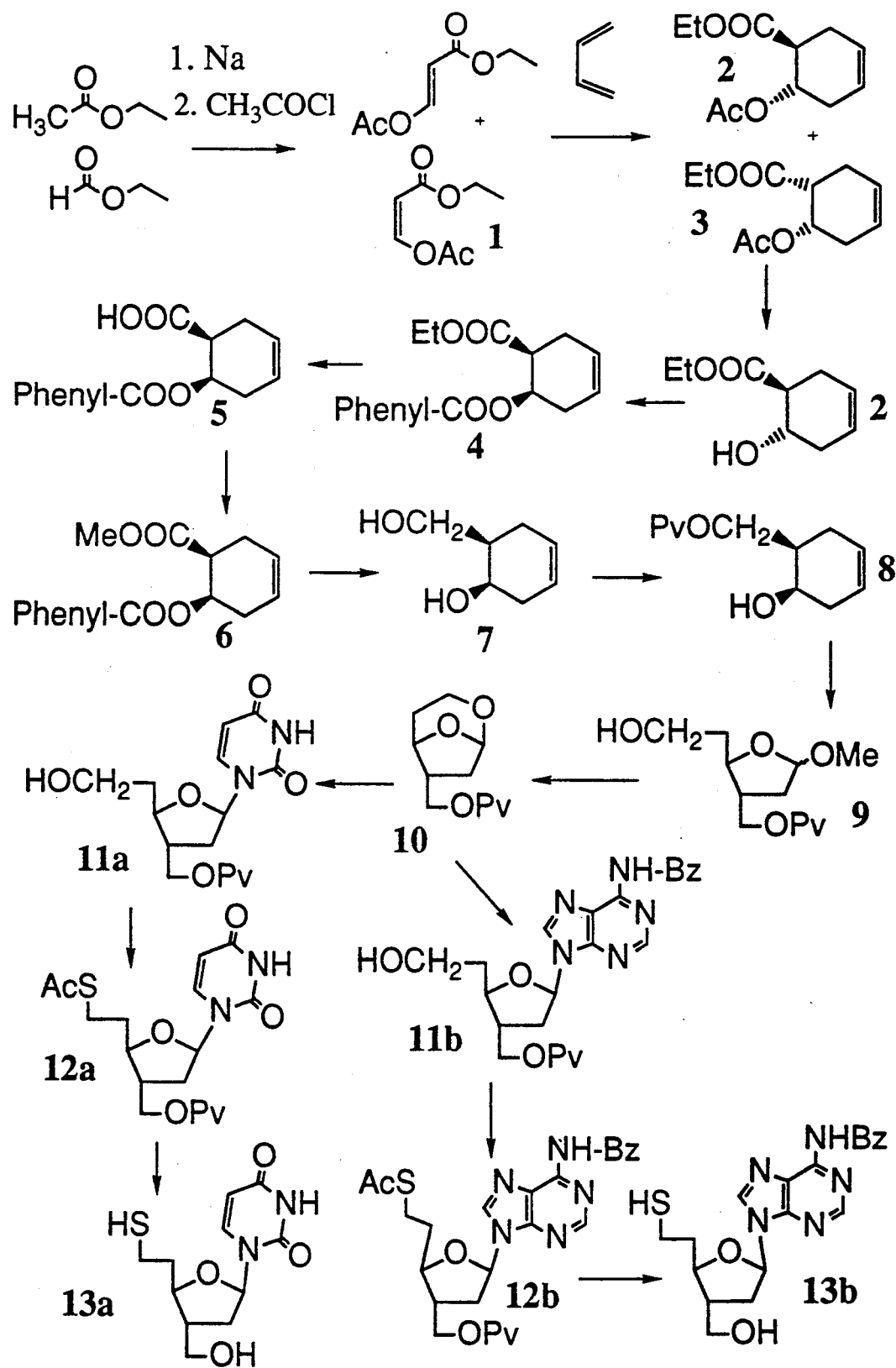
FIG. 7 depicts a synthetic route for preparing rigid oxycyclic isosteric nucleoside analog building blocks that proceeds via a derivatized cyclohexene ring, corresponding to the procedures disclosed in Examples 1 and 2.

Example 1 (FIG. 7)

Rigid, Isosteric Building Block, Heteroatom in Linker Ethyl 3-Acetoxyacrylate (1)

A mixture of EtOAc (100.0 g, 1.136 mol) and ethyl formate (80.7 g, 1.136 mol) was slowly added with stirring at RT to sodium wire (26.0 g, 1.130 mol) in dry ether (400 ml). The reaction mixture was stirred for 20 hours, and the sodium salt of ethyl-3-hydroxyacrylate was isolated by centrifugation as brownish precipitate (yield after drying, 92 g). The sodium salt was finely ground, suspended in ether (400 ml), and the solution cooled to 0° C. Acetyl chloride (55.25 g, 0.70 4 mol) was added dropwise at 0° C. to this suspension. The reaction mixture was stirred at RT for 24 hours, then poured into aqueous saturated sodium bicarbonate (200 ml) at 0° C. The organic phase was separated, washed with water (5×200 ml), dried (magnesium sulfate) and the solvents evaporated. The resulting oil was distilled under vacuum to yield ethyl-3-acetoxyacrylate (20% overall yield) in a cis:trans mixture (1:1.4 by NMR and gas chromatography).

1-Acetoxy-2-carboethoxycyclohex-4-ene (cis and trans) 3 and 2

Ethyl 3-acetoxyacrylate (1, 11.0 g, 69.6 mmol) and butadiene (30.0 ml, 0.8 mol) were dissolved in toluene (distilled from calcium hydride, 25 ml); the mixture was placed in a 500 ml autoclave at −78° C. The autoclave was sealed, and then heated for 15 hours at 170° C. The autoclave was cooled and opened, the contents centrifuged, and the gummy residue extracted with toluene (3×100 ml). The toluene was removed under vacuum, and the mixture of cis and trans 1-acetoxy-2-carboethoxycyclohex-4-ene (3 and 2) was isolated by distillation (101° C. at 2 torr).

Trans 1-Hydroxy-2-carboethoxycyclohex-4-ene 2a

Sodium hydride (200 mg) was added to a mixture of the cis and trans isomers of ethyl 1-acetoxy-2-carboethoxycyclohex-4-ene (1.60 g, 7.55 mmol) in absolute ethanol (50 ml), and the mixture was stirred for 1 hour at RT. The reaction mixture was neutralized with Dowex W 50 cation exchange resin (acid form), the resin removed by filtration, the solvents removed under vacuum, and the residue chromatographed on silica gel (hexane:EtOAc 7:3, Rf=0.40) to yield 1.2 g (94%) trans 1-hydroxy-2-carboethoxycyclohex-4-ene (IR CCl$_4$, 1732 cm$^{-1}$).

Ethyl cis-2-benzoyloxy-cyclohex-4-enecarboxylate 4

DEAD (2.06 g, 11.8 mmol) was added dropwise to a solution of triphenylphosphine (3.08 g, 11.8 mmol) in THF (35 ml) at 0° C. over a period of 5 min. Trans 1-Hydroxy-2-carboethoxycyclohex-4-ene 2a (1.00 g, 5.88 mmol in 5 ml THF) was then added slowly, the mixture was stirred for 5 min, and then benzoic acid (1.44 g, 11.8 mmol, in 5 ml THF) was added. The mixture was stirred at RT for 2 hours. Solvents were evaporated, an the residue purified by chromatography on silica gel (EtOAc:hexane 2:8 as eluant). The product was then distilled under vacuum to yield ethyl cis-2-benzoyloxy-cyclohex-4-enecarboxylate (4, 1.1 g, 71%).

(1S,2R)-1-Benzoyloxycyclohex-4-ene-2-carboxylic acid

Pig liver esterase (16 mg, 2000 units) was added to ethyl cis-2-benzoyloxy-cyclohex-4-enecarboxylate (4) suspended in a mixture of t-butanol and water (1:9) at pH 7, and the progress of the enzymic hydrolysis was followed with an autotitrator (maintaining the pH at 7) with 0.5N NaOH). After 36% of the starting material had been hydrolyzed, the reaction was quenched with CH$_2$Cl$_2$ (3 ml) and extracted with ether (3×30 ml). The ethereal layers were dried (magnesium sulfate), and the solvent removed under vacuum to yield 1.9 g (63%) of a mixture of (1S,2R)- and (1R,2S) 1-benzoyloxy-2-carboethoxycyclohex-4-ene. The pH of the aqueous phase was adjusted to 2 and extracted with ether (3×30 ml). The ethereal layers were dried (magnesium sulfate), and the solvent removed under vacuum to yield 982 mg (35.8%) crude (1S,2R)-1-benzoyloxycyclohex-4-ene-2-carboxylic acid (5). This was shown to be essentially free of its enantiomer via gas chromatographic analysis of the 1-norborneol ester, and by NMR in the presence of a europium chiral shift reagent.

(1R,2S)-1-Benzoyloxycyclohex-4-ene-2-carboxylic acid 5

Pig liver esterase (6 mg, 800 units) was added to cis 1-benzoyloxy-2-carboethoxycyclohex-4-ene suspended in a mixture of t-butanol and water (1:9) at pH 7, and the mixture incubated at RT for 15 hours. Following work-up as described above, the first ethereal extract yielded 1.46 g (48%) of (1R,2S) 1-benzoyloxy-2-carboethoxycyclohex-4-ene >97% enantiomerically pure ([α]$_D$, (c 3.1, acetone)=+105.6

Methyl cis-2-benzoyloxy-cyclohex-4-enecarboxylate 6

A solution of 1-benzoyloxycyclohex-4-ene-2-carboxylic acid (5, 160 mg, 0.645 mmol) in ether (5 ml) is treated with a solution of diazomethane (excess) in ether. The solvent was removed under vacuum to yield methyl cis-2-benzoyloxy-cyclohex-4-enecarboxylate (6, 168 mg, 100%) as a colorless oil. When enantiomerically pure starting material was used, the product of this reaction was >97% enantiomerically pure. [α]$_D$(c 6.35, acetone)=−89.5 for the 1S,2R isomer).

cis-2-Hydroxymethyl-cyclohex-4-eneol 7

Methyl cis-2-benzoyloxy-cyclohex-4-enecarboxylate (6, 1.1 g, 4.19 mmol) was dissolved in THF (10 ml), and the solution added to a dispersion of lithium aluminum hydride (0.35 g, 9.15 mmol) in THF (30 ml) at −78° C. The mixture was warmed to RT and stirred for 5 hours. The mixture was then cooled to −15° C., and then diluted successively with water (0.35 ml), 15% NaOH (0.35 ml), and water (1.05 ml). The precipitate was removed by filtration, washed with EtOAc, and the solvent removed under vacuum. The residual oil was purified by chromatography on silica gel (EtOAc, Rf=0.28) to yield cis 2-hydroxymethylcyclohex-4-eneol (7, 419 mg, 78%) as a colorless oil.

2-Pivaloyloxymethyl-cyclohex-4-eneol 8

Pivaloyl chloride (1.036 g, 1.1 equivalents) was added at −20° C. to a solution of 2-hydroxymethyl-cyclohex-4-eneol (7, 1.00 g, 7.81 mmol) in pyridine (10 ml). The reaction mixture was kept at −20° C. for 20 hours, diluted with methanol and ether (50 ml), and the organic layer extracted with 20 ml portions of 10% HCl containing copper sulfate until the blue color in the organic layer had disappeared. The ethereal layer was dried (magnesium sulfate), the solvent removed under vacuum, and the residue chromatographed on silica gel (hexane:EtOAc 7:3, Rf=0.43) to yield 2-pivaloyloxymethyl-cyclohex-4-eneol (8, 1.54 g, 93%) as a colorless oil. (IR, $CCl_4$ 1730 $cm^{-1}$). 3,4-trans 1-Methoxy-3-pivaloyloxymethyl-4-(2'-hydroxyethyl)-tetrahydrofuran 9 and 1-Methoxy-3-pivaloyloxymethyl-4-(2',2'-dimethoxyethyl)-tetrahydrofuran.

2-Pivaloyloxymethyl-cyclohex-4-eneol (8, 6.327 g, 29.8 mmol) was dissolved in methanol (250 ml), cooled to −78° C., and then treated with ozone (ca. 30 min) until the solution was blue. After excess ozone was removed in a stream of nitrogen (45 min), dimethylsulfide (10 ml) was added, and the reaction was warmed to RT and stirred in the dark for 7 days. Analysis by gas chromatography showed a 3:1 mixture of the 2' aldehyde and its corresponding dimethyl acetal. The mixture was cooled to 0° C., and $NaBH_4$ (1.00 g) was added in small portions. After 20 min., 5% HCl (20 ml) was added, half of the methanol evaporated, the mixture was diluted with water (100 ml), and the mixture was extracted with $CH_2Cl_2$ (3×100 ml). The organic layer was dried (magnesium sulfate), the solvent evaporated under vacuum, and the residue chromatographed on silica gel (hexane:EtOAc 6:4) to yield a mixture of 3,4-trans 1-methoxy-3-pivaloyloxymethyl-4-(2'-hydroxyethyl)-tetrahydrofuran (9, 4.85 g, 62%, IR, $CCl_4$, 1732 $cm^{-1}$) and 1-methoxy-3-pivaloyloxymethyl-4-(2',2'-dimethoxyethyl)-tetrahydrofuran (1.845 g, 20%, IR, $CCl_4$, 1732 $cm^{-1}$) as colorless oils and as mixtures of anomers.

exo-6-Pivaloyloxymethyl-2,8-dioxa-[1.2.3]bicyclooctane 10

A solution of 3,4-trans 1-methoxy-3-pivaloyloxymethyl-4-(2'-hydroxyethyl)-tetrahydrofuran (9, 500 mg) in toluene (10 ml) with Dowex W 50 cation exchange resin (acid form) was refluxed for 3 hours. The resin was removed by filtration, and the solvent evaporated under vacuum to yield exo-6-pivaloyloxymethyl-2,8-dioxa-[1.2.3)-bicyclooctane (10, 434 mg, 99%) as colorless crystals (from hexane). NMR ($CDCl_3$) 1.20 (s, 9H), 1.57 (s, br, 1H), 1.67 (ddd, J=14,3,2.5 Hz, 1H), 2.30 (m, 2H), 2.51 (m, 1H), 3.81–4.08 (m, 4H), 4.32 (s, br, 1H), 5.44 (d, J=5 Hz)

3',5'-Bishomo-2-deoxyuridine-3'O-pivalate 11a

To a solution of bis-trimethylsilyloxypyrimidine in acetonitrile was added exo-6-pivaloyloxymethyl-2,8-dioxa-[1.2.3]-bicyclooctane (10, 200 mg, 0.877 mmol) in acetonitrile (1 ml). A solution of trimethylsilyltriflate (0.191 ml, 1.2 equivalents) in dichloroethane (1 ml) was then added, and the mixture stirred at RT for 15 hours. The mixture was then poured onto ice cold saturated aqueous sodium bicarbonate, the aqueous layer was extracted with $CH_2Cl_2$ (3×10 ml), the solvent removed under vacuum, and the residue chromatographed on silica gel ($CHCl_3$:methanol 9:1, Rf 0.20) to yield a mixture of anomers of 3',5'bishomo-2-deoxyuridine-3'-pivalate as a white foam (11a, 1:1 mixture, 156 mg, 52%). The beta anomer (11a) is the preferred anomer. NMR ($CDCl_3$) 1.20 (2 s, 9H), 1.78–2.50, 2.74 (mm, 6H), 3.84, 4.00, 4.13 (3 m, 5H), 5.77 (d, J=10 Hz, 1H), 6.17 (m, 1H), 7.46 (2 d, J=10 Hz, 1H), 9.59 (s, br, 1H, exchangeable). Anal calc. for $C_{16}H_{24}N_2O_6$: C, 56.46%; H, 7.11%; N, 8.23%. Found C, 55.97%; H, 6.98%; N, 8.00%.

5'-Deoxy-5'-methylcarboxythio-3',5'-bishomo-2-deoxyuridine-3'-pivalate 12a

DEAD (0.03 ml, 0.18 mmol) was added at 0° C. to a solution of triphenylphosphine (47 mg, 0.18 mmol) in THF (0.5 ml). The mixture is stirred for 30 min. 3',5'-bishomo-2-deoxyuridine-3'-pivalate (11a, 0.09 mmol) dissolved in THF (0.5 ml) is then added together with thioacetic acid (0.013 ml, 0.18 mmol)) in THF (0.5 ml). The reaction mixture is stirred at 0° C. for 1 hour, and then for another hour at RT. The solvents are then evaporated under vacuum, and the residue chromatographed on silica gel (20 g, EtOAc eluant) to yield 5'-deoxy-5'-methylcarboxythio-3',5'-bishomouridine-3'-pivalate.

This compound could be conveniently stored. Free thiol-alcohol building block (13a) for use in the synthesis of oligonuclectide analogs is prepared immediately prior to coupling by reduction of 12a with lithium triethylborohydride in THF.

Example 2 (FIG. 7)

Rigid, Isosteric Building Block, Heteroatom in Linker

3',5'-Bishomo-2-deoxy-N-benzoyladenine-3'-pivalate 11b

N-Benzoyladenine (483 mg, 2 mmol) was suspended in acetonitrile (5 ml), and N-methyl-N-trimethylsilyltrifluoroacetamide (1.31 ml, 6.34 mmol) was added to give a clear solution. Exo-6-pivaloyloxymethyl-2,8-dioxa-[1.2.3]-bicyclooctane (10, 500 mg, 1.92 mmol) (from Example 1) was then added, and the mixture stirred for 1 hour at RT. Stannic chloride (0.32 ml, 1.5 equivalents) was then added, and stirring continued for 5 hours. The reaction was quenched with cold saturated sodium bicarbonate (10 ml), and the products extracted with EtOAc and flashed with methanol chloroform (1:9) pivalate 11b.

5'-Deoxy-5'-methylcarboxythio-3',5'-Bishomo-2-deoxy-N-benzoyladenosine-3'-pivalate 12b DEAD (0.03 ml, 0.18 mmol) was added at 0° C. to a solution of triphenylphosphine (47 mg, 0.18 mmol) in THF (0.5 ml). The mixture is stirred for 30 min. 3',5'-Bishomo-2-deoxy-N-benzoyladenosine-3'-pivalate (11b, 0.09 mmol) dissolved in THF (0.5 ml) is then added together with thioacetic acid (0.013 ml, 0.18 mmol)) in THF (0.5 ml). The reaction mixture is stirred at 0° C. for 1 hour, and then for another hour at RT. The solvents are then evaporated under vacuum, and the residue chromatographed on silica gel (20 g, EtOAc eluant) to yield 5'-deoxy-5'-methylcarboxythio-3',5'-bishomo-2-deoxy-N-benzoyladenosine-3'-pivalate 12b.

This compound could be conveniently stored. Free thiol-alcohol building block (13b) is prepared immediately prior to coupling by reduction of 12b with lithium triethylborohydride in THF.

Figure 8:
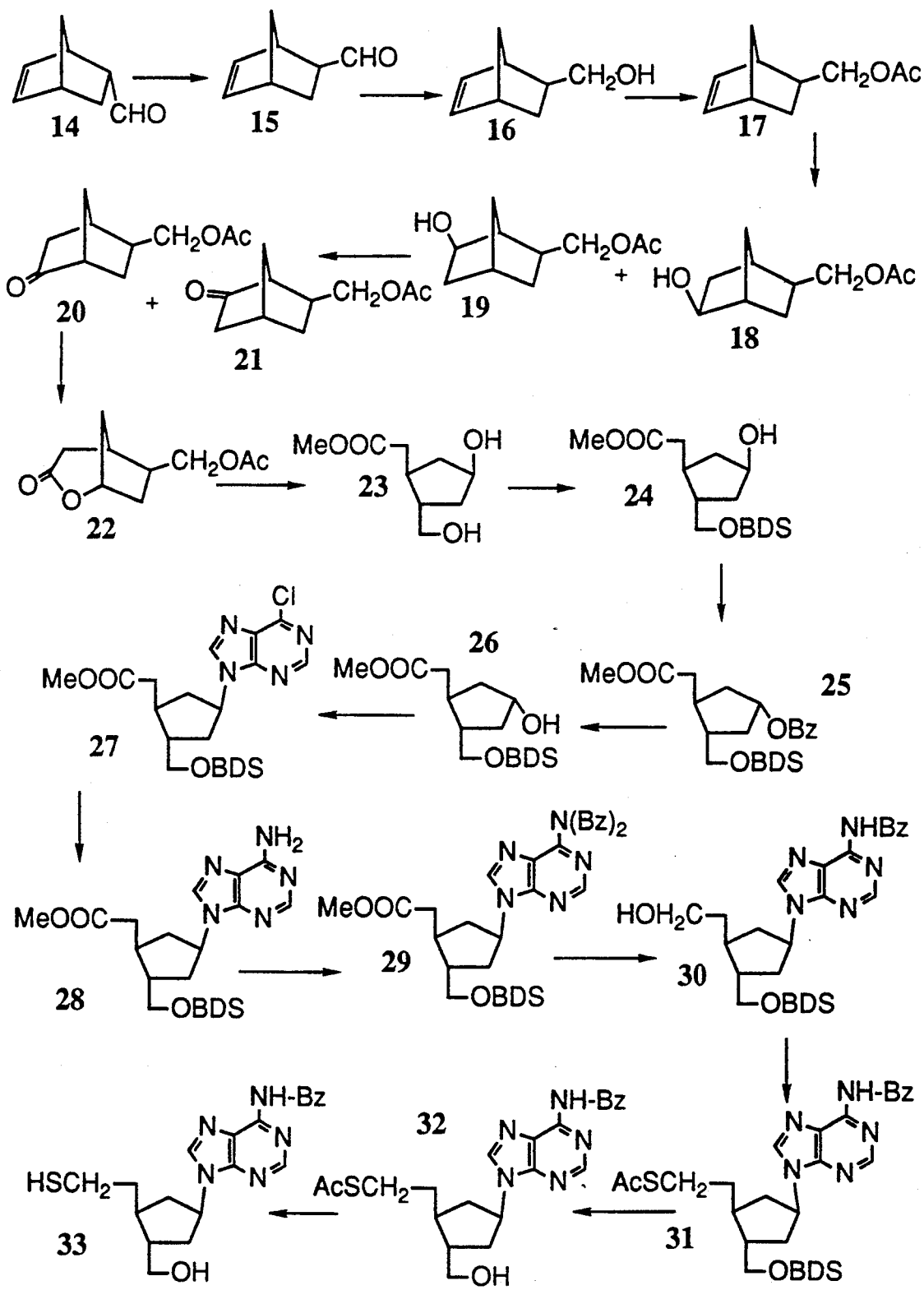
FIG. 8 depicts a synthetic route for preparing rigid oxycyclic isosteric nucleoside analog building blocks that proceeds via a derivatized norbornene system, corresponding to the procedures disclosed in Example 3.

Example 3 (FIG. 8)

Rigid, Isosteric Building Block, No Heteroatom in Linker exo Norbornene-2-carboxaldehyde 15

Lithium hydroxide (960 mg, 20 mmol, in 20 ml water) was added to a solution of norbornene-2-carboxaldehyde (14, Fluka, 24.4 g, 0.2 mol in 500 ml of THF), and the mixture was stirred overnight under reflux. The reaction mixture was then neutralized (to pH 7.5) at 0° C. with concentrated HCl, and the THF/water azeotrope removed under reduced pressure. The residue was chromatographed on Kieselgel (pentane:ether (30:1) as eluant) to yield exo norbornene-2-carboxaldehyde (15, 11.0 g, 45%).

exo Norbornene-2-methanol 16

A solution of sodium borohydride (1.7 g, 45 mmol) in 20 ml of 2N NaOH was added dropwise at 0° C. over a period of 1 hour to a solution of exo norbornene-2-carboxaldehyde (15, 11 g, 90 mmol) in methanol (50 ml). The mixture was allowed to warm to RT, and was stirred for 1 hour. The progress of the reaction was monitored by thin layer chromatography. After the reaction was complete, the mixture was acidified at 0° C. by slow addition of concentrated HCl, and the product extracted twice with ether (500 ml). The ether was washed with aqueous sodium bicarbonate, dried ($Mg_2SO_4$), and evaporated to yield exo norbornene-2-methanol (16, 10.8 g, 97% yield).

exo Norbornene-2-methanol acetate 17

Exo norbornene-2-methanol (16, 9.82 g, 79 mmol) was dissolved in pyridine (13 ml) containing dimethylaminopyridine (0.75 g, 1.6 mmol). The mixture was cooled to 0° C. under argon, and acetic anhydride (10 ml, 103 mmol) was added dropwise. After addition, the solution was allowed to stir one half hour at RT. Ice (50 g) was added, and the mixture was acidified at 0° C., and extracted twice with ether. The extracts were washed (dilute HCl, then sodium bicarbonate), dried and evaporated. Exo norbornene-2-methanol acetate (17, 10.3 g, 56 mmol, 71%) was recovered by distillation under vacuum (87° C. at 12 torr).

exo 5- and 6-Hydroxy-2-exo-norbornanmethanol acetate 18 and 19

Diborane, generated by the treatment of sodium borohydride (2.3 g, 67 mmol) in THF (40 ml) with trifluoroboron etherate (15 ml) over a period of 30 min was passed into a solution of exo-norbornene-2-methanol acetate (17, 10.3 g, 62 mmol) in THF (60 ml) at 0° C. After the addition was complete, the reaction was quenched with water (10 ml) and 2N NaOH (10 ml). Then hydrogen peroxide (8 ml, 30%) was added at 0° C. After one hour at 50° C., sodium chloride was added and the mixture extracted with EtOAc. Normal work up yielded a crude mixture of exo 5- and 6-hydroxy-exo-norbornene-2-methanol acetates (18 and 19, 12 g), which were not separated at this point.

This same intermediate can be prepared in optically active form from optically active exo t-butyl 5-norbornene-2-carboxylate synthesized via an asymmetric Diels-Alder reaction (Oppolzer, W.; Chapuis, C.; Kelly, M. J., *Helv. Chem. Acta* 1983, 66, 2358-2361) followed by reduction with $LiEt_3BH$ and hydroboration by the method described above.

5- and 6-keto-exo-norbornane-2-methanol acetate 20 and 21

Pyridinium chlorochromate (21.5 g, 100 mmol) was stirred with Celite (15 g) and methylene chloride (140 ml) at RT. To the suspension was added a mixture of 5 and 6 hydroxy-exo-norbornane-2-methanol acetate (18 and 19, 12 g, 62 mmol) in methylene chloride (70 mmol) dropwise over a period of 30 min. The mixture was stirred for an hour at RT, at which point the dark brown suspension was filtered through silica gel (60 g). Chromatography yielded a crude mixture of 5- and 6-keto-exo-norbornane-2-methanol acetate (20 and 21, 12.5 g). This mixture was separated by silica gel chromatography (column diameter 5 cm×45 cm, ca. 400 g Kieselgel) using pentane:ether (1:1) as an elution solvent. After distillation, the desired 5-keto-exo-norbornane-2-methanol acetate crystallized (20, 4.36 g, 40% yield) upon cooling.

3-Keto-2-oxa-6-exo-bicyclo-[3.2.1]-octanmethanol acetate 22

5-Keto-exo-norbornane-2-methanol acetate (21, 3.3 g, 18 mmol) was stirred with sodium acetate (9 g, water-free), hydrogen peroxide (27 ml, 30%), and acetic acid (9 ml) at 5° C. in the dark for 40 hours. The reaction was quenched by the addition of sodium sulfite (50 ml of a 10% aqueous solution) at 0° C. The product was extracted twice with EtOAc (600 ml). The extract was washed with the sodium sulfite solution, then with sodium bicarbonate solution (50 ml, saturated), then with sodium chloride solution (saturated), dried and evaporated. The product was chromatographed on silica (380 g, ether) to yield 3-keto-2-oxa-6-exo-bicyclo-[3.2.1.]-octanmethanol acetate (22, 2.4 g, 12 mmol, 67%, mp 55°–56° C.).

Methyl 2-trans-hydroxymethyl-4-cis-hydroxycyclopentaneacetate 23

3-Keto-2-oxa-6-exo-bicyclo-[3.2.1.]-octanmethanol acetate (22, 2.4 q, 12 mmol) was dissolved in methanol (100 ml) at 0° C., and a solution of sodium metal (560 mg, 24 mmol) in methanol (50 ml) was added. After refluxing overnight, the mixture was acidified at 0° C. with acetic acid (to pH 8.5). After filtration and evaporation, the product was chromatographed on silica (350 g ) with ether:ethanol (19:1) as eluant to yield methyl-2-hydroxymethyl-4-hydroxycyclopentane-1-acetate (23, 2.12 9, 94% yield) as a colorless oil.

Methyl 2-trans-t-butyldiphenylsilyloxymethyl-4-cis-hydroxycyclopentaneacetate 24

Methyl 2-trans-hydroxymethyl-4-cis-hydroxycyclopentaneacetate (23, 430 m9, 2.3 mmol) and imidazole (340 mg, 5mmol) was dissolved in dimethylformamide (2.5 ml) at 0° C. To the mixture was added t-butyldiphenylsilyl chloride (692 mg, 0.64 ml, 2.52 mmol) at 0° C. The mixture was then warmed to RT and stirred for 2 hours. The excess silyl chloride was hydrolyzed with water, and the product extracted twice with EtOAc. The extracts were washed with saturated sodium chloride solution, dried, and evaporated to yield methyl 2-trans-t-butyldiphenylsilyloxymethyl-4-cis-hydroxycyclopentaneacetate (24, 640 mg, 67%) as a colorless liquid.

Methyl 2-trans-t-butyldiphenylsilyloxymethyl-4-trans-benzoyloxycyclopentaneacetate 25

Triphenylphosphine (2.9 g, 11.1 mmol) and benzoic acid (1.35 g, 11.1 mmol) in THF (74 ml) were added to a solution of methyl 2-trans-t-butyldiphenylsilyloxymethyl-4-cis-hydroxycyclopentaneacetate (24, 3.16 g, 7.4 mmol). The mixture was cooled to 0° C. with stirring, and then DEAD (1.87 ml, 11.1 mol, in 15 ml THF)

was added. The mixture was stirred a half hour, yielding a clear slightly yellow solution. The solvents were evaporated under vacuum, and the residue chromatographed on silica gel (pentane:ether (2:1) as eluant) to yield methyl 2-trans-t-butyldiphenylsilyloxymethyl-4-trans-benzoyloxycyclopentaneacetate (25, 4.01 g).

Methyl 2-trans-t-butyldiphenylsilyloxymethyl-4-trans-hydroxycyclopentaneacetate 26

To a solution of methyl 2-trans-t-butyldiphenylsilyloxymethyl-4-trans-benzoyloxycyclopentaneacetate (25, 4.01 g, 7.4 mmol) in methanol (35 ml) at 0° C. was added under argon a solution of sodium metal (0.19 g, 7.7 mmol) in methanol (25 ml). The mixture was stirred under argon overnight. The pH of the mixture was then adjusted to 8.5 with acetic acid, the mixture filtered, the solvents evaporated, and the products chromatographed on silica with pentane:ether (1:2) as eluant to yield methyl 2-trans-t-butyldiphenylsilyloxymethyl-4-trans-hydroxycyclopentaneacetate (26, 2.74 g, 87% yield).

Methyl 2-trans-t-butyldiphenylsilyloxymethyl-4-cis-(6-chloropurin-9-yl)-cyclopentaneacetate 27

To a solution of triphenylphosphine (730 mg, 2.8 mmol) and 6-chloropurine (430 mg, 2.8 mmol) in dry THF (16 ml) was added a solution of DEAD (0.42 ml, 2.8 mmol) in dry THF (3.5 ml). The mixture was stirred for 2 hours at RT. To the solution was added methyl 2-trans-t-butyldiphenylsilyloxymethyl-4-trans-hydroxycyclopentaneacetate (26, 800 mg, 1.9 mmol) in THF (9 ml). After the reaction was complete, the solvents were evaporated, and the residue purified by chromatography on silica (60 g) with pentane:ether (1:5) as eluant to yield methyl 2-trans-t-butyldiphenylsilyloxymethyl)-4-cis-(6-chloropurin-9-yl) cyclopentaneacetate (27, 820 mg, 78%).

Methyl 2-trans-t-butyldiphenylsilyloxymethyl-4-cis-(aden-9-yl)-cyclopentaneacetate 28

Aqueous ammonium hydroxide (25%, 40 ml) was added to a solution of methyl 2-trans-t-butyldiphenylsilyloxymethyl-4-cis-(6-chloropurin-9-yl)-cyclopentaneacetate (27, 480 mg, 0.85 mmol) in dioxane (40 ml) at RT. Air was excluded with a balloon filled with $NH_3$. After 30 min, the mixture was heated at 60° C., and stirred for 24 hours. Dioxane (100 ml) was then added, and the azeotrope removed by evaporation. The residue was chromatographed on Kieselgel using ether:ethanol (4:1) as eluant, to yield methyl 2-trans-t-butyldiphenylsilyloxymethyl-4-cis-(aden-9-yl)-cyclopentaneacetate (28, 330 mg, 71%).

Methyl 2-trans-t-butyldiphenylsilyloxymethyl-4-cis-(N.N-dibenzoyladen-9-yl)-cyclopentaneacetate 29

Benzoyl chloride (0.6 ml, 4.7 mmol) was added slowly to a solution of methyl 2-trans-t-butyldiphenylsilyloxymethyl-4-cis-(aden-9-yl)-cyclopentaneacetate (28, 318 mg, 0.59 mmol) in pyridine (4 ml) and $CH_2Cl_2$ at 0° C. The mixture was stirred 2 hours at RT. The excess benzoyl chloride was hydrolyzed with water at 0° C., and the product was extracted twice with ether. The extracts were washed with an aqueous solution of copper sulfate (10%) and brine, dried, and evaporated. After silica chromatography with ether as eluant, methyl 2-trans-t-butyldiphenylsilyloxymethyl-4-cis-(N,N-dibenzoyladen-9-yl)-cyclopentaneacetate was isolated (29, 381 mg, 86%) as a colorless foam.

2-(Trans-t-butyldiphenylsilyloxymethyl)-4-cis-(N-benzoyladen-9-yl)-cyclopentaneethanol 30

A solution of lithium triethylborohydride (1M in THF, 0.85 ml, 0.85 mmol) was added over a period of a half hour to a solution of methyl 2-trans-t-butyldiphenylsilyloxymethyl 4-cis-(N.N-dibenzoyladen-9-yl)-cyclopentaneacetate (129 mg, 0.17 mmol) in dry THF (3 ml) at −18° C. under argon. The mixture was stirred for 30 min at 10° C. More reducing agent (0.2 ml) was then added at 0° C., and stirring continued at RT for another half hour. The reaction mixture was then hydrolyzed with saturated ammonium chloride (0.5 ml), evaporated, and the residue chromatographed on silica gel (ether:ethanol 9:1 as eluant) to yield 2-(trans-t-butyldiphenylsilyloxymethyl)-4-cis-(N-benzoyladen-9-yl)-cyclopentaneethanol (30, 83 mg, 78%).

2-(Trans-t-butyldiphenylsilyloxymethyl)-4-cis-(N-benzoyladen-9-yl)-cyclopentaneethanethiol S-acetate 31

DEAD (0.03 ml, 0.18 mmol) was added to a solution of triphenylphosphine (47 mg, 0.18 mmol) in THF (0.5 ml) at 0° C., and the mixture was stirred for 30 min. Solutions of 2-(trans-t-butyldiphenylsilyloxymethyl)-4-(cis-N-benzoyladen-9-yl) cyclopentaneethanol (30, 55 mg, 0.09 mmol) in THF (0.5 ml) and thioacetic acid (0.013 ml, 0.18 mmol) in THF (0.5 ml) were then added. The reaction mixture was stirred at 0° C. for 1 hour, and then for another hour at RT. The solvents were then evaporated, and the residue chromatographed on silica gel (20 g) with EtOAc as eluant, to yield 2-(trans-t-butyldiphenylsilyloxymethyl)-4-cis-(N-benzoyladen-9-yl)-cyclopentaneethanethiol S-acetate (31, 48 mg, 80%) as a colorless foam.

2-(Trans-t-hydroxymethyl)-4-cis-(N-benzoyladen-9-yl)-cyclopentaneethanethiol S-acetate 32

Tetrabutylammonium fluoride (trihydrate, 70 mg, 0.22 mmol) was added to 2-(trans-t-butyldiphenylsilyloxymethyl)-4-cis-(N-benzoyladen-9-yl)-cyclopentaneethanethiol S-acetate (31, 98 mg, 0.145 mmol) dissolved in dry THF (3 ml). The mixture was stirred at RT for 15 hours. The solvents were then evaporated under vacuum, and the residue chromatographed on silica gel (ether:ethanol 4:1 as eluant) to yield 2-(trans-t-hydroxymethyl)-4-cis-(N-benzoyladen-9-yl)-cyclopentaneethanethiol S-acetate (32, 90 mg, 77%) as a white foam. NMR (DMSO-$d_6$) 1.57–1.70 (m, 1H); 1.79–2.31 (m, 6H); 2.33 (s, 3H); 2.39–2.46 (m, 1H); 2.84–2.91 (m, 2H); 3.38–3.49 (m, 2H); 4.68–4.72(m, 1H); 4.87–4.98 (m, 1H); 7.52–7.57 (m, 2H); 7.62–7.67(m, 1H); 8.04–8.06 (m, 2H); 8.60 (s, 1H); 8.73 (s, 1H); 11.16 (s, br., 1H). Anal calc. for $C_{22}H_{25}N_5O_3S$ C 60.12%, H 5.73%, N 15.93%; found C 59.12%, H 5.74%, N 15.72%.

This compound could be conveniently stored. Free thiol-alcohol building block (33) is prepared immediately prior to coupling by hydrolysis of this compound under basic conditions.

Figure 9:
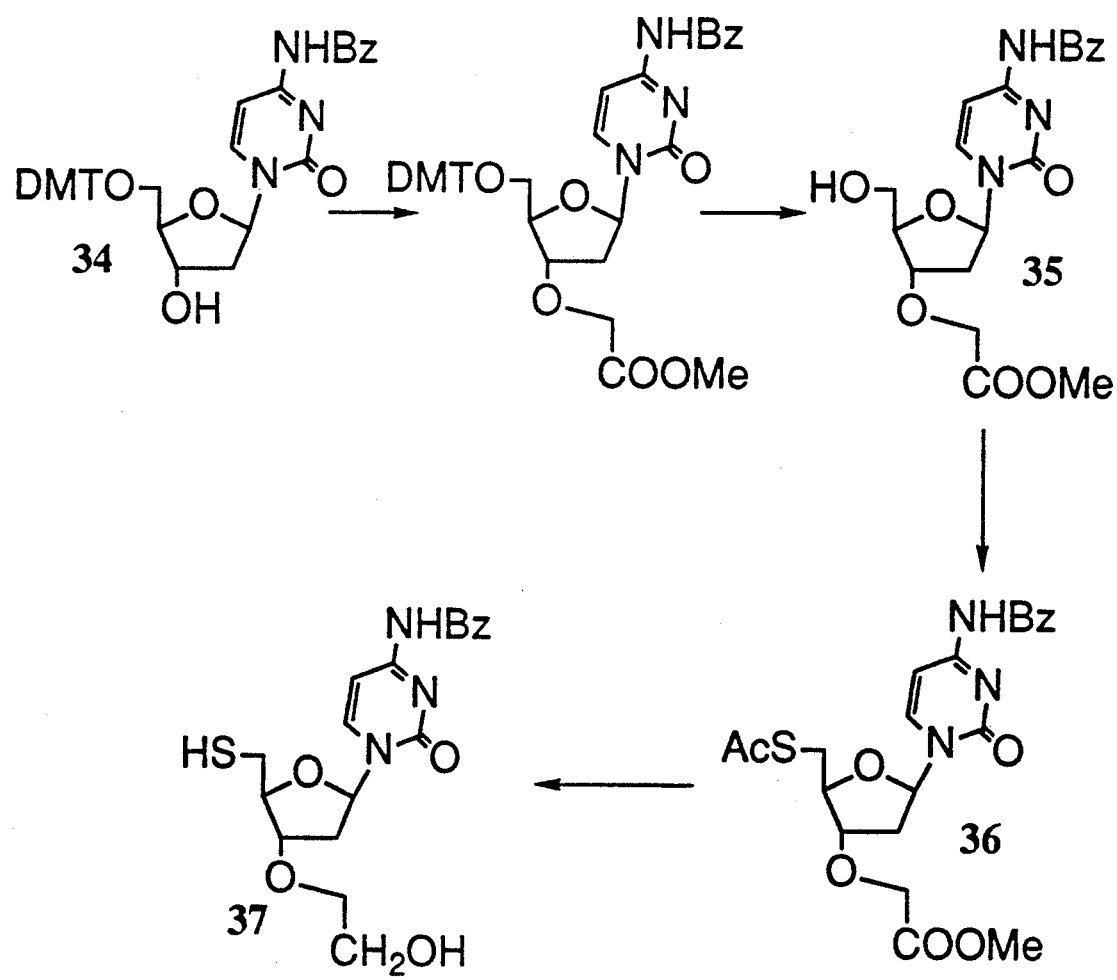
FIG. 9 depicts a synthetic route for preparing rigid oxycyclic nucleoside analog building blocks that begins with a natural nucleoside, corresponding to the procedures disclosed in Example 4.

Example 4 (FIG. 9)

Rigid, Non-isosteric, Heteroatom in Linker

N-Benzoyl-3-O-methylcarboxyethyl-2'-deoxycytosine

A standardized solution of the dimethylsulfoxide anion in dimethylsulfoxide (5.1 mmol) is added to a solution of N-benzoyl-5'-dimethoxytrityl-2-deoxycytosine (34, Aldrich, 5 mmol) in anhydrous dimethylsulfoxide (10 ml) at 0° C. Methyl bromoacetate (5.2 mmol) is then slowly added to this reaction mixture over a period of 30 min. The reaction mixture is then allowed to warm to room temperature overnight, is quenched with dilute aqueous acid, and N-benzoyl-3-O-methylcarboxyethyl-2'-deoxycytosine (35) is isolated by extraction into ether.

N-benzoyl-3-O-methylcarboxyethyl-2'5'-dideoxy-5'-mercaptocytosine S-acetate 36

DEAD (0.03 ml, 0.18 mmol) is added at 0° C. to a solution of triphenylphosphine (47 mg, 0.18 mmol) in THF (0.5 ml). The mixture is stirred for 30 min. The product from the previous reaction step (35, 0.09 mmol) in THF (0.5 ml) and thioacetic acid (0.013 ml, 0.18 mmol)) in THF (0.5 ml) are then adced to the solution. The reaction mixture is stirred at 0° C. for 1 hour, and then for another hour at RT. The solvents are then evaporated under vacuum, and the residue chromatographed on silica gel (20 g, EtOAc eluant) to yield the S-acetate of N-benzoyl-3-O-methylcarboxyethyl-2',5'-dideoxy-5-mercaptocytosine (36).

This compound can be conveniently stored, and converted to the free thiol-alcohol building block (37) immediately before coupling either by reduction with lithium borohydride in THF or by hydrolysis in base.

Figure 10:
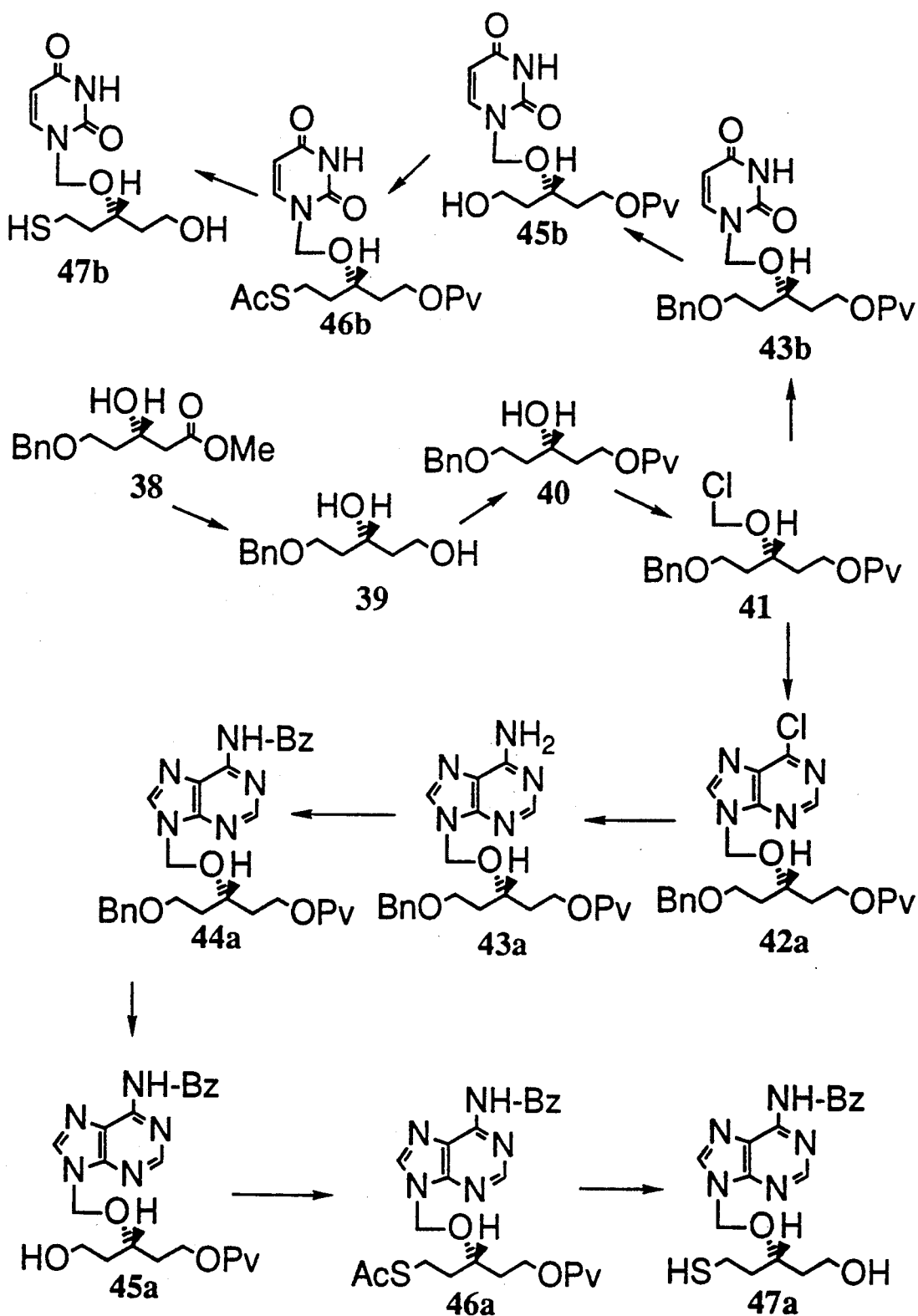
FIG. 10 depicts a synthetic route for preparing flexible nucleoside analog building blocks, corresponding to the procedures disclosed in Examples 5 and 6.

Example 5 (FIG. 10)

Non-rigid, Isosteric, Heteroatom in Linker

5-Benzyloxy-1,3-pentanediol 39

To a solution of methyl 3-(S)-hydroxy-5-benzyloxypentanoate (38, Kitamura, M.; Ohkuma, T.; Inoue, S.; Sayo, N.; Kumobayashi, H.; Akutagawa, S.; Ohta, T.; Takaya, H.; Noyori, R., *J. Am. Chem. Soc.* 1988, 110 629–631) (183 mmol) in anhydrous THF (1 l) is added lithium borohydride (7.7 g, excess) at 0° C. over 15 min. The reaction mixture is stirred at RT for 30 minutes, and then refluxed for 6 hours. The mixture is then cooled to 0° C., diluted with water (60 ml), and stirred overnight at RT. A white precipitate is removed by filtration, the solvent removed in vacuum, and the residue distilled under vacuum to yield 5-benzyloxy-1,3-pentanediol 39.

1-Pivaloyloxy-5-benzyloxy-3-pentanol 40

Pivaloyl chloride (2.070 ml, 17.1 mmol) was added slowly to a solution of 5-benzyloxy-1,3-pentanediol (39, 16.3 mmol) in anhydrous pyridine (35 ml) at −18° C. (dry ice-acetone bath). The mixture was kept without stirring in a −20° freezer for 15 hours. The reaction mixture was then diluted with methanol (1 ml) and CH$_2$Cl$_2$ (50 ml), and extracted with 10% HCl containing copper sulfate (10 g/l) until the blue color in the organic layer was removed. The aqueous layer was re-extracted with methylene chloride, the combined organic layers are dried (magnesium sulfate), the solvent evaporated, and 1-pivaloyloxy-5-benzyloxy-3-pentanol (40) isolated as a colorless oil by flash chromatography on silica gel (hexane/EtOAc 7:3 as eluant; yield 4.05 g, 86% as a colorless oil).

1-Pivaloyloxy-5-benzyloxy-3-O-chloromethyloxypentane 41

1-Pivaloyloxy-5-benzyloxy-3-pentanol (40, 294 mg, 1.0 mmol) was dissolved in dichloroethane (3 ml) together with paraformaldehyde (600 mg, 2.0 mmol). The solution was cooled to 0° C., and HCl gas was passed through the solution until all of the solid had dissolved (ca. 3.5 hours). The clear solution was dried (magnesium sulfate) and the solvent removed under vacuum, to yield 1-pivaloyloxy-5-benzyloxy-3-O-chloromethyloxypentane (41) in essentially quantitative yield as a clear oil.

1'-Pivaloyloxy-5'-benzyloxy-3'-((6-chloro)purin-9-yl)-methyloxypentane 42a

6-Chloropurine (663 mg, 3.7 mmol) was dissolved in a mixture of dimethylformamide (10 ml) and triethylamine (0.57 ml). The mixture was cooled to 0° C., and as solution of 1-pivaloyloxy-5-benzyloxy-3-O-chloromethyloxypentane (41, from 1.09 g of 1-pivaloyloxy-5-benzyloxy-3-pentanol) in dry dimethylformamide (10 ml) was added slowly over a period of 15 min. After addition was complete, the mixture was allowed to warm to RT overnight. The solvent was removed under vacuum, and the residue purified by flash chromatography on silica gel to yield 880 mg (52%) of a colorless oil consisting of a 20:1 mixture of the N$^9$ (42a) and (presumably) the N$^7$ isomer of the desired product.

1'-Pivaloyloxy-5'-benzyloxy-3'-(aden-9-yl)-methyloxypentane 43a

A solution of 1'-pivaloyloxy-5'-benzyloxy-3'-((6-chloro)purin-9-yl)-methyloxypentane (42a, 795 mg, 1.725 mmol) in methanol (50 ml) was saturated at 0° C. with ammonia, and the mixture heated in a sealed glass tube at 110° C. for 20 hours. The tube was then cooled to 0° C., its contents transferred to a flask, and the solvent evaporated. The residue was chromatographed on silica gel (CH$_2$Cl$_2$/methanol 9:1 as eluant) to yield 1'-pivaloyloxy-5'-benzyloxy-3'-(aden-9-yl)-methyloxypentane (43a, 600 mg, 79%) as a colorless oil.

1'-Pivaloyloxy-5'-benzyloxy-3'-(6-N-benzoyladen-9-yl)-methyloxypentane 44a

To a suspension of 1'-pivaloyloxy-5'-benzyloxy-3'-(aden-9-yl)-methyloxypentane (43a, 390 mg) in dry pyridine (20 ml) was added trimethylchlorosilane (5 fold excess), and the mixture stirred for 15 min. Benzoyl chloride (1 ml) was then added, and the mixture stirred for 2.5 hours. The mixture was then cooled on an ice bath, and diluted with water (10 ml). After 5 min, 29% aqueous ammonia (10 ml) was added, and the mixture stored at room temperature for 30 min. The reaction mixture was then evaporated to near dryness, and the residue dissolved in saturated sodium bicarbonate solution (15 ml), and the solution extracted three times with methylene chloride. The extracts were dried (magnesium sulfate) and flashed with hexane:EtOAc (1:1) as eluant to yield 1'-pivaloyloxy-5'-benzyloxy-3'-(6-N-benzoyladen-9-yl)-methyloxypentane (44a, 305 mg, 56%).

5'-Pivaloyloxy-3'-(6-N-benzoyladen-9-yl)-methyloxypentan-1-ol 45a

1'-Pivaloyloxy-5'-benzyloxy-3'-(6-N-benzoyladen-9-yl)-methyloxypentane (44a, 380 mg, 0.456 mmol) is dissolved in a cyclohexene:ethanol (3:10) mixture, palladium hydroxide (300 mg, 20% on carbon) is added, and the reaction mixture is heated at 80° C. overnight. The reaction mixture is filtered through Celite, the Celite is washed with ethanol, and the combined filtrates is evaporated to yield an oil. The oil is purified by flash chromatography on silica gel to yield 5'-pivaloyloxy-3'-(6-N-benzoyladen-9-yl)-methyloxypentan-1-ol (45a).

5'-Pivaloyloxy-3'-(6-N-benzoyladen-9-yl)-methyloxypentan-1-thiol S-acetate 46a

DEAD (0.03 ml, 0.18 mmol) was added at 0° C. to a solution of triphenylphosphine (47 mg, 0.18 mmol) in THF (0.5 ml). The mixture is stirred for 30 min. 5'-Pivaloyloxy-3'-(6-N-benzoyladen-9-yl)-methyloxypentan-1-ol (45a, 0.09 mmol) in THF (0.5 ml) and thioacetic acid (0.013 ml, 0.18 mmol)) in THF (0.5 ml) are then added to the solution. The reaction mixture is stirred at 0° C. for 1 hour, and then for another hour at RT. The solvents are then evaporated under vacuum, and the residue chromatographed on silica gel (20 g, EtOAc eluant) to yield 5'-pivaloyloxy-3'-(6-N-benzoyladen-9-yl)-methyloxypentan-1-thiol S-acetate (46a).

This compound could be conveniently stored, and hydrolyzed in base to the free thiol-alcohol building block (47a) immediately before coupling.

Example 6 (FIG. 10)

Non-rigid, Isosteric, Heteroatom in Linker

The uracil analog was prepared analogously. The chloromethyl ether (41, 3.6 g)) was added to a refluxing mixture of $CH_2Cl_2$ (20 ml), tetrabutylammonium iodide (13.5 mg) and 2.5 ml of 2,4-bis(trimethylsilyloxy)pyrimidine was refluxed for 1 hour. The reaction mixture was diluted with methanol, the solvents removed, and the product purified by flash chromatography to yield 1'-pivaloyloxy-5'-benzyloxy-3'-(urid-3-yl)methyloxypentane (43b, 1.04 g).

1'-Pivaloyloxy-5'-benzyloxy-3'-(urid-3-yl)methyloxypentane (43b, 710 mg) dissolved in a mixture of ethanol:cyclohexene (28 ml, 5:2) and treated with palladium oxide (400 mg) as described above yielded 5'-pivaloyloxy-3'-(urid-3-yl)methyloxypentan-1-ol To a solution of this product (45b, 100 mg, 0.304 mmol) in THF (2 ml) was added thioacetic acid (30 mg), triphenylphosphine 111 mg, and DEAD 80 ul using the procedure described above to yield 5'-pivaloyloxy-3'-(uridyl-1-yl)-methyloxypentane-1-thiol S-acetate (46b, 91 mg, 77%).

As above, this compound could be conveniently stored, and hydrolyzed in base to the free thiol-alcohol building block (47b) immediately before coupling.

Figure 11:
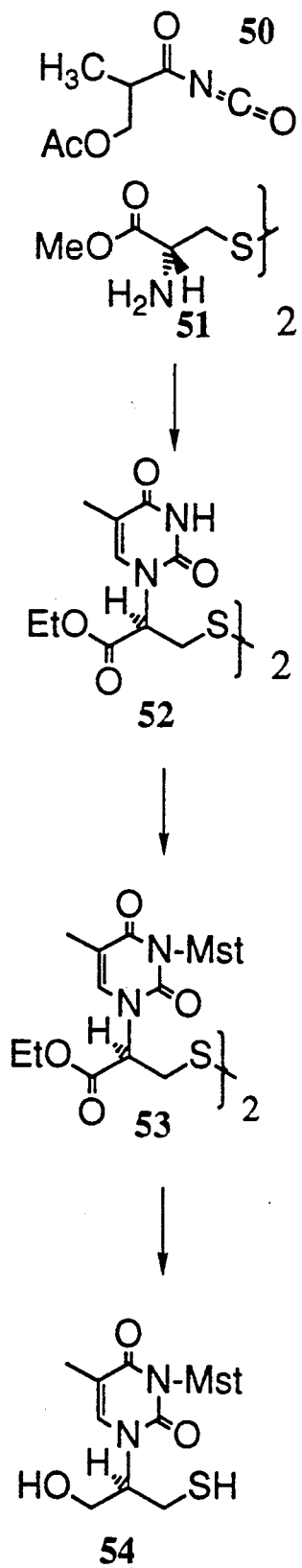
FIG. 11 depicts a synthetic route for preparing flexible nucleoside analog building blocks via a path that constructs a pyrimidine ring, corresponding to the procedures disclosed in Example 7.

Example 7 (FIG. 11)

Non-rigid, Not Isosteric, No Heteroatom in Linker, Class (0,1,1)

2-methyl-3-ethoxyacryloyl isocyanate 50

Silver isocyanate (4.166 g, 27.8 mmol, dried in the dark over phosphorus pentoxide at 135° C.) was suspended in anhydrous benzene (20 ml). To the suspension was added 2-methyl-3-ethoxyacryloyl chloride (2.369 9, 16 mmol) (Shealy, Y. F.; O'Dell, C. A.; Thorpe, M. C., *J. Heterocyclic Chem.* 1981, 18 383-389) in benzene (15 ml). The mixture was heated at reflux for a half hour, and then cooled slowly to RT over a period of 2.5 hours. This procedure yielded a solution of 2-methyl-3-ethoxyacryloyl isocyanate 50 in benzene.

Disulfide of ethyl 2'-(uridyl-1-yl)-3-mercaptopropionate 52

In a separate flask, the dimethylester of L-cystine (51, commercial as hydrochloride, 1.703 g, 5.0 mmol), triethylamine (1.478 9, 14.6 mmol), and pyrrolidinopyridine (319 mg, 2.2 mmol), was dissolved in dimethylformamide (30 ml). The solution of 2-methyl-3-ethoxyacryloyl isocyanate 50 in benzene prepared above was then added to this solution at −12° C. over a period of 45 minutes, and the mixture was stirred at RT for an additional 12 hours. The solvents were then removed under vacuum (0.01 torr), and the residue chromatographed over Kieselgel ($CH_2Cl_2$-ethanol as eluant) to yield 3.24 g of an amide intermediate.

The amide intermediate (6.584 g, 11.37 mmol) was dissolved in ethanol (40 ml) and 2N sulfuric acid (40 ml), and the mixture refluxed for 5 hours. Most of the solvent was removed at reduced pressure, the residue was suspended in ethanol (30 ml) and benzene (200 ml), and the water removed by azeotropic distillation. The solvents were removed, and dissolved in $CH_2Cl_2$. The organic solution was extracted with saturated aqueous sodium bicarbonate, saturated aqueous sodium chloride, and dried. The disulfide of ethyl 2'-(uridyl-1-yl)-3-mercaptopropionate (52, 5.966 g) was isolated following removal of the solvent.

The pyrimidine ring was protected by an N-mesityl group (Welch, C. J.; Chattopadhyaya, J. B. *Acta Chem. Scand.* B, 1983, 37 147-150) through reaction with the hexachloroantimoniate salt of the mesityl cation in $CH_2Cl_2$ with pyridine (2 equivalents) to yield a suitably protected building block precursor (53). This compound could be conveniently stored, and the free thiol-alcohol building block (54) produced immediately prior to coupling by reduction with lithium triethylborohydride using the following procedure.

Building Block 54

To a solution under argon of disulfide 53 (1.088 g, 2.1 mmol) in THF (10 ml) at −18° C. was added 20 ml of a 1M solution of lithium triethylborohydride in THF. The reaction mixture was stirred at −18° C. for 30 minutes, and then allowed to warm to RT. After 24 hours, 10 ml of a saturated aqueous solution of ammonium chloride was added, and the building block (54) purified by chromatography on Kieselgel ($CH_2Cl_2$-ethanol as eluant).

Figure 12:
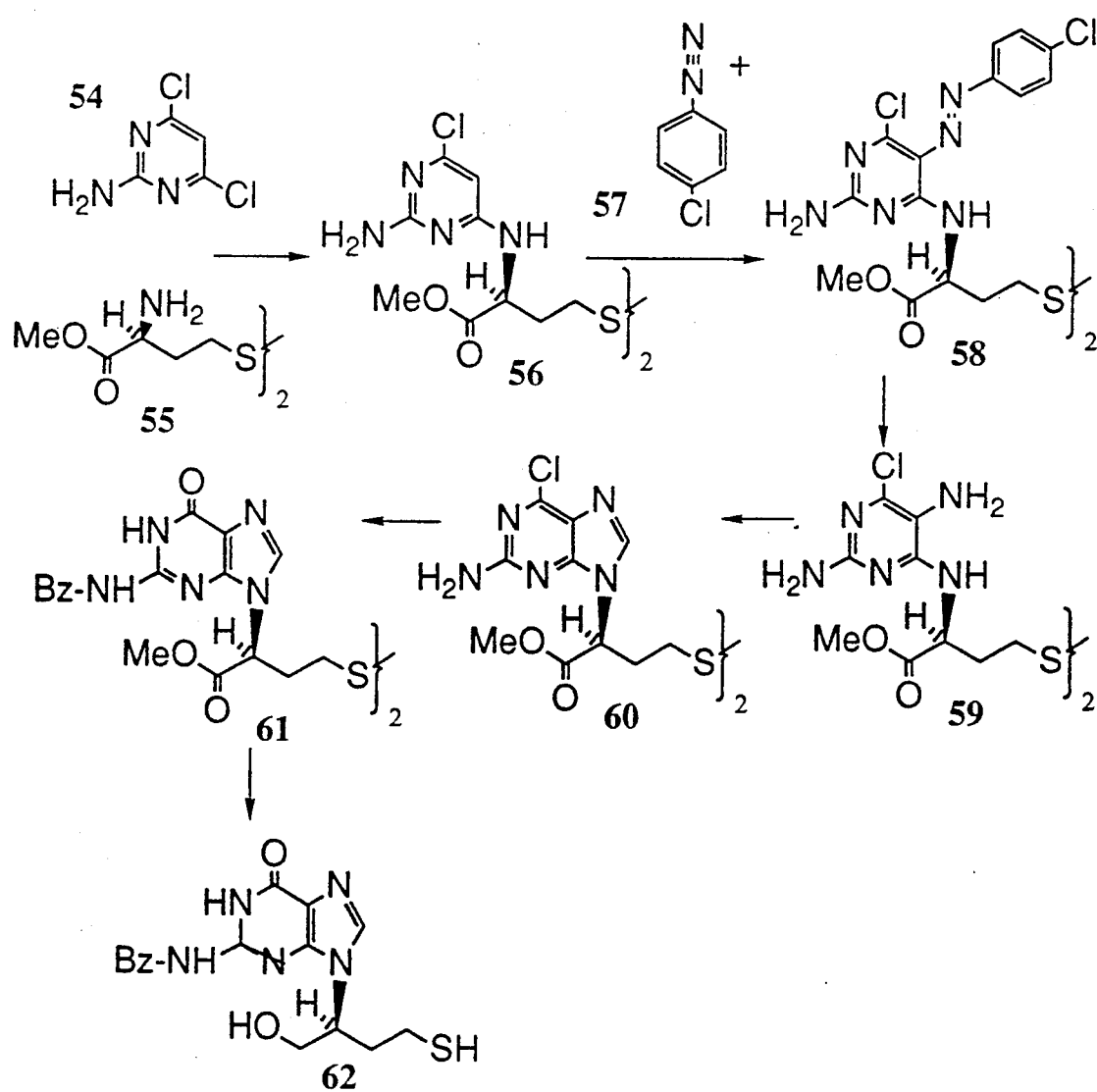
FIG. 12 depicts a synthetic route for preparing flexible nucleoside analog building blocks via a path that constructs a purine ring, corresponding to the procedures disclosed in Example 8.

Example 8 (FIG. 12)

Non-rigid, Not Isosteric, No Heteroatom in Linker, Class (0,1,2)

Disulfide of N-(2-amino-4-chloropurin-9-yl)-homocysteine 60

A mixture of 2-amino-4,6-dichloropyrimidine (54, commercial, 99%, 13.6 g, 83 mmol, 3 fold excess), the dimethyl ester of homocystine (55, 27 mmol), triethylamine (10 ml) (350 ml) is refluxed in ethanol for 24 hours. The reaction mixture is then placed in a freezer, where unreacted 2-amino-4,6-dichloropyrimidine slowly separates from the cold mixture and is removed by filtration. The filtrate is concentrated under reduced pressure to yield a partially solid residue.

4-Chlorobenzene diazonium chloride (57) is prepared at 0° C. from 10.6 g (83 mmol) 4-chloroaniline, 23 ml HCl (12N), and sodium nitrite (6.3 g, 90 mmol) in 78 ml water (Y. F. Shealy, C. A. O'Dell, G. Arnett *J. Med. Chem.* 1987, 30 1090-1094). The cold solution of the diazonium salt is added dropwise over a period of min to a stirred solution (at RT) of product of previous reaction, sodium acetate trihydrate (150 g), acetic acid (375 ml), and water (400 ml). The mixture is stirred overnight at RT. Diazo intermediate 58 is collected as a precipitate by filtration.

The diazo compound (58, 14 mmol) is suspended in ethanol (120 ml), water (120 ml) and acetic acid (12 ml) under nitrogen at 70° C. Zinc dust (11.5 9) is added slowly (over 1 hour). Heating is continued for another 1.5 hours. The mixture is filtered under nitrogen, the precipitate washed with ethanol, the filtrate and washings combined and concentrated to 0.25 of the original volume under vacuum. 4-Chloroaniline is removed from the aqueous mixture by extraction with ether, the pH raised to 6.0 with NaOH (2N), and triamine 59 is collected as a precipitate, washed (cold water) and dried.

To the triamine (59, 2.5 mmol) in cold dimethylacetamide (6 ml) is added triethylorthoformate (5.2 ml, freshly distilled) and HCl (12N, 0.25 ml). The mixture is stirred overnight under nitrogen at RT, concentrated under vacuum, dissolved in 88% formic acid (15 ml), refluxed overnight, and concentrated in vacuum. Remaining solvent is removed by several evaporations of methanol. The disulfide of N-(2-amino-4-chloropurin-9-yl)-homocysteine 60 is then precipitated from cold ammonia-methanol (10% ammonia).

This product could be converted to the protected precursor of the guanosine analog building block 61 by acidic hydrolysis (Y. F. Shealy, C. A. O'Dell, G. Arnett, J. Med. Chem. 1987, 30 1090-1094), followed by benzoylation by the procedure described above. Product 61 could be conveniently stored, and converted to the thiol-alcohol building block (62) immediately before coupling by reduction with lithium borohydride.

Figure 13:
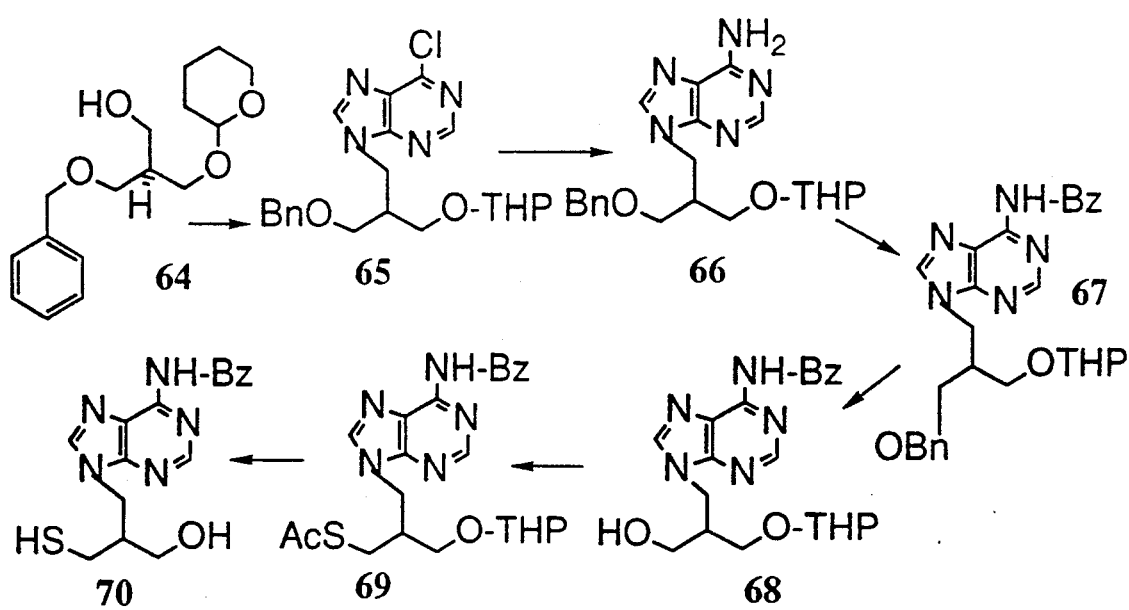
FIG. 13 depicts a synthetic route for preparing flexible nucleoside analog building block, corresponding to the procedures disclosed in Example 9.

Example 9 (FIG. 13)

Non-rigid, Not Isosteric, No Heteroatom in Linker, Class (1,1,1)

2-(N-Benzoyl-adenyl-9-yl)methyl-3-mercaptopropanol 70

A solution of triphenylphosphine (730 mg, 2.8 mmol) and 6-chloropurine (430 mg, 2.8 mmol) in dry THF (16 ml) is added to a solution of DEAD (0.42 ml) in dry THF (3.5 ml). The mixture was stirred for 2 hours at RT. To the solution is added enantiomerically pure 2(R)-benzyloxymethyl-3-(tetrahydropyran-2-yloxy)-1-propanol (64, 1.9 mmol; Haruda, T.; Hayashiya, T.; Wada, I.; Iwa-ake, N.; Oku, A. *J. Am. Chem. Soc.* 1987, 109 527-532) in THF (9 ml). After the reaction is complete, the solvents were evaporated, and the residue containing intermediate 65 purified by chromatography.

The intermediate 65 is dissolved in methanol saturated at 0° C. with ammonia, and the mixture heated in a sealed glass tube at 110° C. for 20 hours. The tube is then cooled to 0° C., its contents transferred to a flask, and the solvent evaporated. The residue is chromatographed on silica gel to yield 9-((2(R)-benzyloxymethyl-3-tetrahydropyran-2-yloxy)-propan-1-yl)-adenine (66). To a suspension of 66 (400 mg) in dry pyridine (20 ml) is added trimethylchlorosilane (5 fold excess), and the mixture stirred for 15 min. Benzoyl chloride (1 ml) was then added, and the mixture stirred for 2.5 hours. The mixture is then cooled on an ice bath, and diluted with water (10 ml). After 5 min, 29% aqueous ammonia (10 ml) is added, and the mixture stored at room temperature for 30 min. The reaction mixture is then evaporated to near dryness, the residue dissolved in saturated sodium bicarbonate solution (15 ml), and the solution extracted three times with methylene chloride. The extracts are dried (magnesium sulfate) and flashed with hexane:EtOAc (1:1) as eluant to yield N-benzoyl 9-((2(R)-benzyloxymethyl-3-tetrahydropyran-2-yloxy)-propan-1-yl)-adenine 67).

Intermediate 67 (0.456 mmol) is dissolved in a cyclohexene:ethanol (3:10) mixture together with palladium hydroxide (300 mg, 20% on carbon). The reaction mixture is heated at 80° C. overnight, then filtered through Celite. The Celite is washed with ethanol, and the combined filtrates were evaporated to yield an oil. The oil is purified by flash chromatography on silica gel to yield N-benzoyl 9-((2(R)-hydroxymethyl-3-tetrahydropyran-2-yloxy)-propan-1-yl)-adenine 68.

DEAD (0.03 ml, 0.18 mmol) is added at 0° C. to a solution of triphenylphosphine (47 mg, 0.18 mmol) in THF (0.5 ml). The mixture is stirred for 30 min. The product of the previous reaction (68, 0.09 mmol) in THF (0.5 ml) and thioacetic acid (0.013 ml, 0.18 mmol)) in THF (0.5 ml) are then added to the solution. The reaction mixture is stirred at 0° C. for 1 hour, and then for another hour at RT. The solvents are then evaporated under vacuum, and the residue chromatographed on silica gel to yield N-benzoyl 9-((2(R)-acetylthiomethyl-3-tetrahydropyran-2-yloxy)-propan-1-yl)-adenine (69).

This compound is conveniently stored, and the free thiol-alcohol building block (70) prepared by hydrolysis of 69 in acid and then base immediately before coupling.

Figure 14:
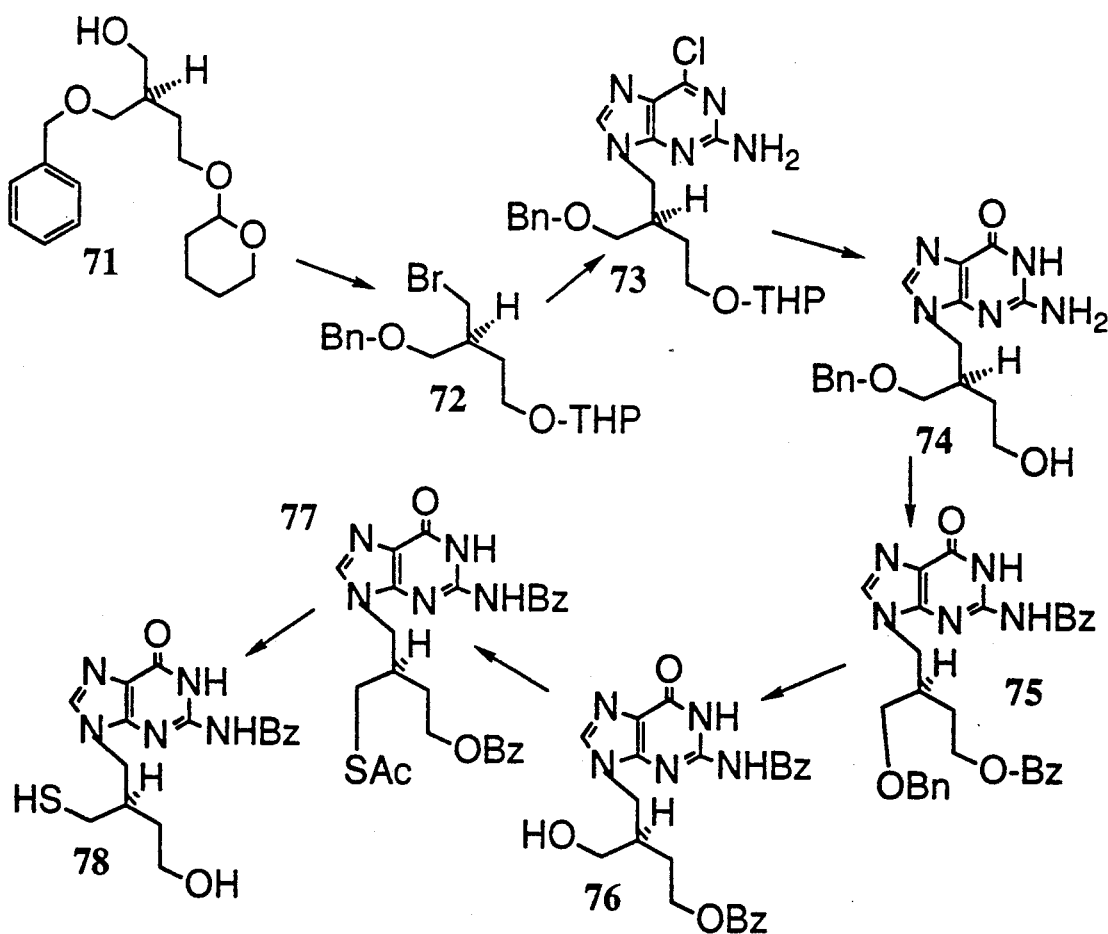
FIG. 14 depicts a synthetic route for preparing flexible nucleoside analog building blocks, corresponding to the procedures disclosed in Example 10.

Example 10 (FIG. 14)

Non-rigid, Not Isosteric, No Heteroatom in Linker class (1,2,1)

2-(N-Benzoyl-guanin-9-yl)methyl-3-mercaptopropanol 78

Enantiomerically pure 2(R)-benzyloxymethyl-4-(tetrahydropyran-2-yloxy)-1-butanol (71, 1.9 mmol; Harnden, M. R.; Jarvest, R. L.; *Tetrahedron Lett.* 1985 26 4265-4268; Haruda, T.; Hayashiya, T.; Wada, I.; Iwa-ake, N.; Oku, A. *J. Am. Chem. Soc.* 1987, 109 527-532) in dimethylformamide is added to a solution of triphenylphosphine and carbon tetrabromide in dimethylformamide to yield 1-bromo-2(R)-benzyloxymethyl-4-(tetrahydropyran-2-yloxy)-1-butane (72. To a solution of 72 in dimethylformamide is added 2-amino-6-chloropurine. After stirring at room temperature (8 hours), 9-((2(R)-benzyloxymethyl-4-tetrahydropyran-2-yloxy)-butan-1-yl)-2-amino-6-chloropurine (73) is isolated and purified by chromatography on silica gel. Acid hydrolysis (2N HCl, reflux, 75 min) converts this compound to 9-((2(R)-benzyloxymethyl-4-hydroxy)-butan-1-yl)-guanine (74), which is purified by chromatography on silica gel.

To a suspension of 74 (300 mg) in dry pyridine (20 ml) is added trimethylchlorosilane (5 fold excess), and the mixture stirred for 15 min. Benzoyl chloride (1 ml) was then added, and the mixture stirred for 2.5 hours. The mixture is then cooled on an ice bath, and diluted with water (10 ml). After 5 min, 29% aqueous ammonia (10 ml) is added, and the mixture stored at room temperature for 30 min. The reaction mixture is then evaporated to near dryness, the residue dissolved in saturated sodium bicarbonate solution (15 ml), and the solution extracted three times with methylene chloride. The extracts are dried (magnesium sulfate) and flashed with hexane:EtOAc (1:1) as eluant to yield N-benzoyl 9-((2(R)-benzyloxymethyl-4-benzoyloxy)-butan-1-yl)-guanine (75), which is purified by chromatography on silica gel.

Following the removal of the benzyl protecting group by catalytic reduction as described previously to yield intermediate 76, and conversion of the free hydoxyl group to an acetylthio group as described previously, the S-acetate of 9-((2(R)-mercaptomethyl-4-benzoyloxy)-butan-1-yl)-9uanine (77 is isolated. This compound could be conveniently stored, and the free thiol hydroxy building block (78) obtained by mild alkaline hydrolysis immediately prior to condensation.

Figure 15:
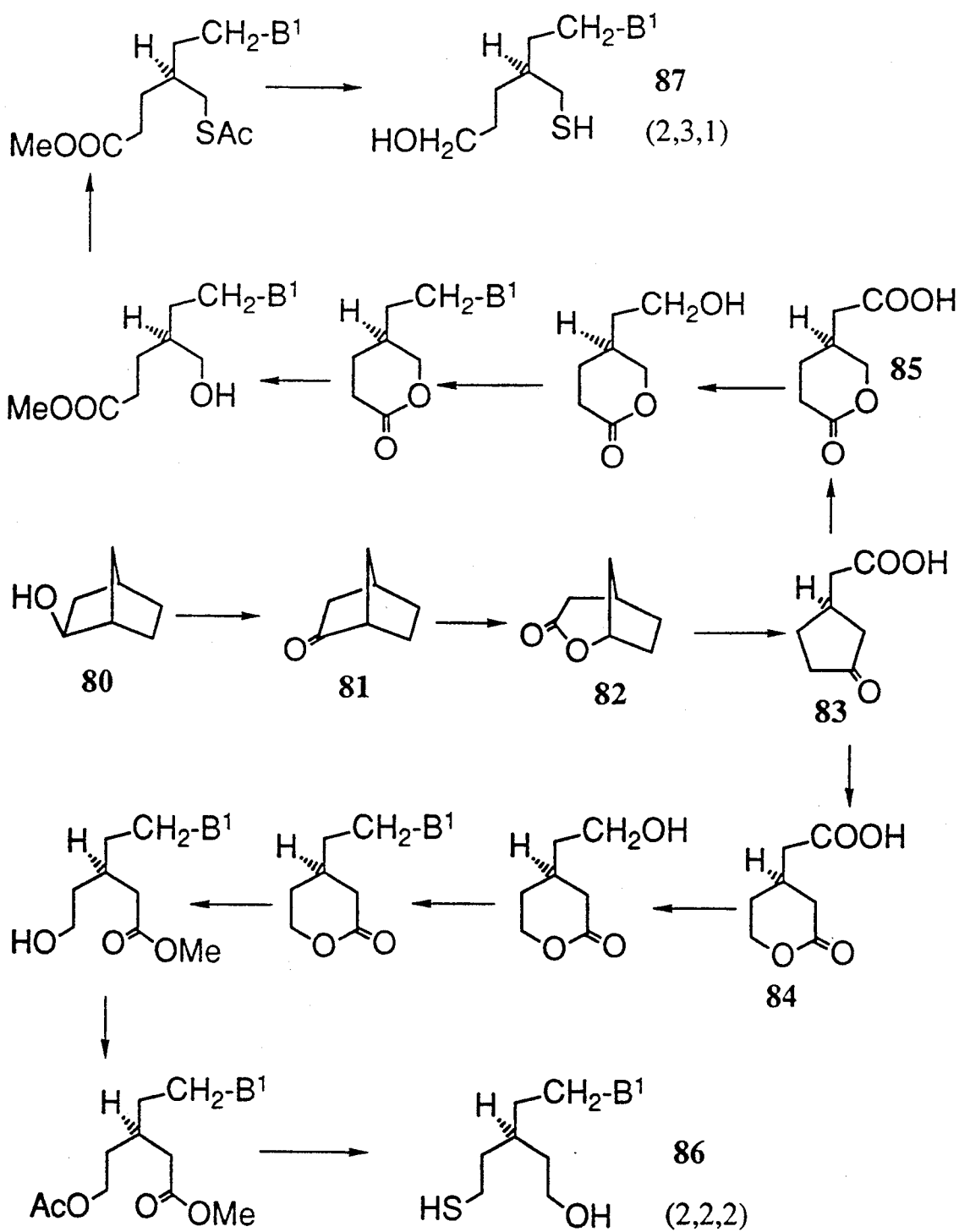
FIG. 15 depicts a synthetic route for preparing flexible nucleoside analog building blocks, corresponding to the procedures disclosed in Example 11.
Figure 16A:
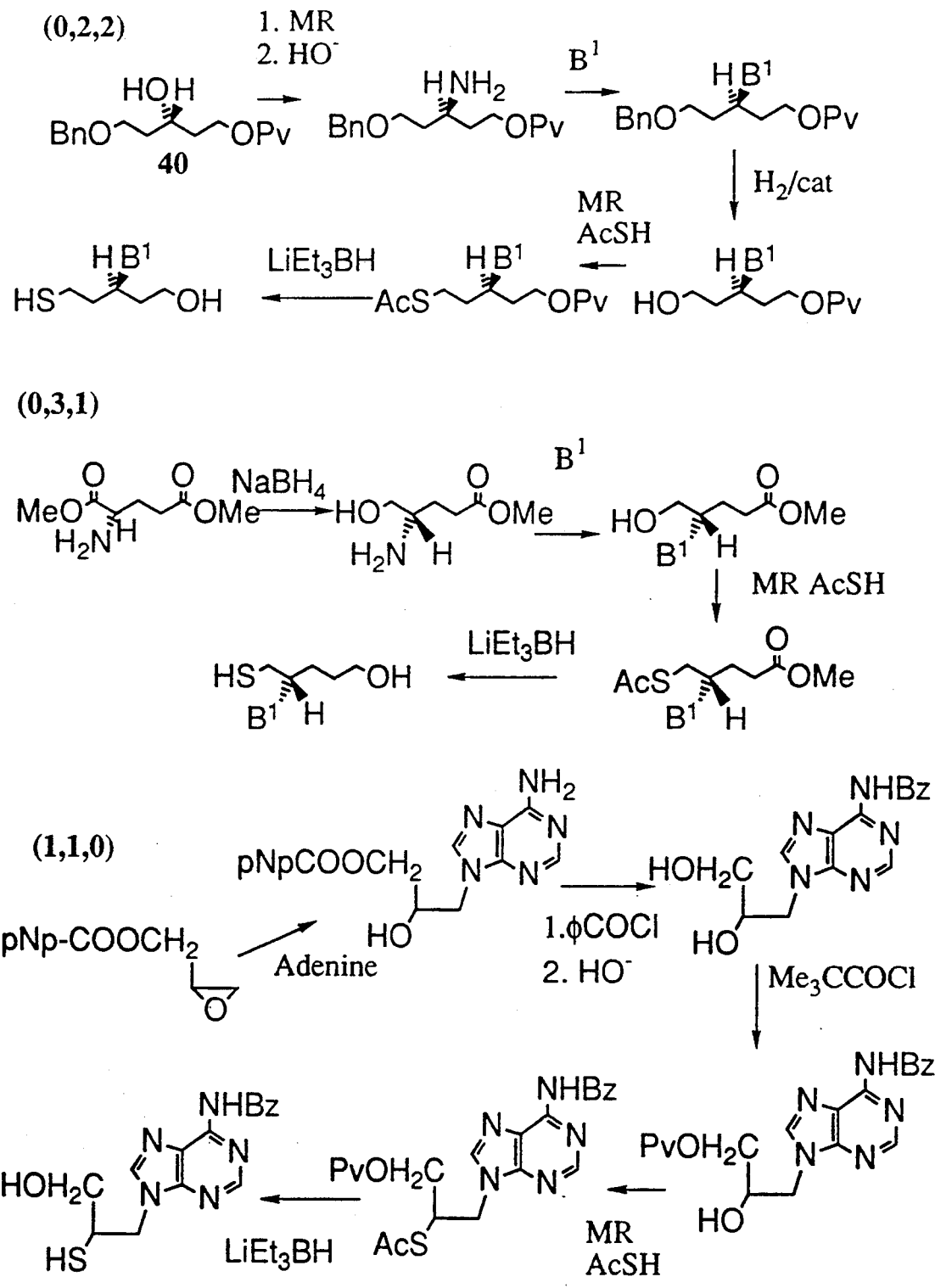
FIG. 16a depicts a synthetic route for preparing flexible nucleoside analog building blocks where the number of atoms joining the base analog to the backbone is 0 or 1.
Figure 16C:
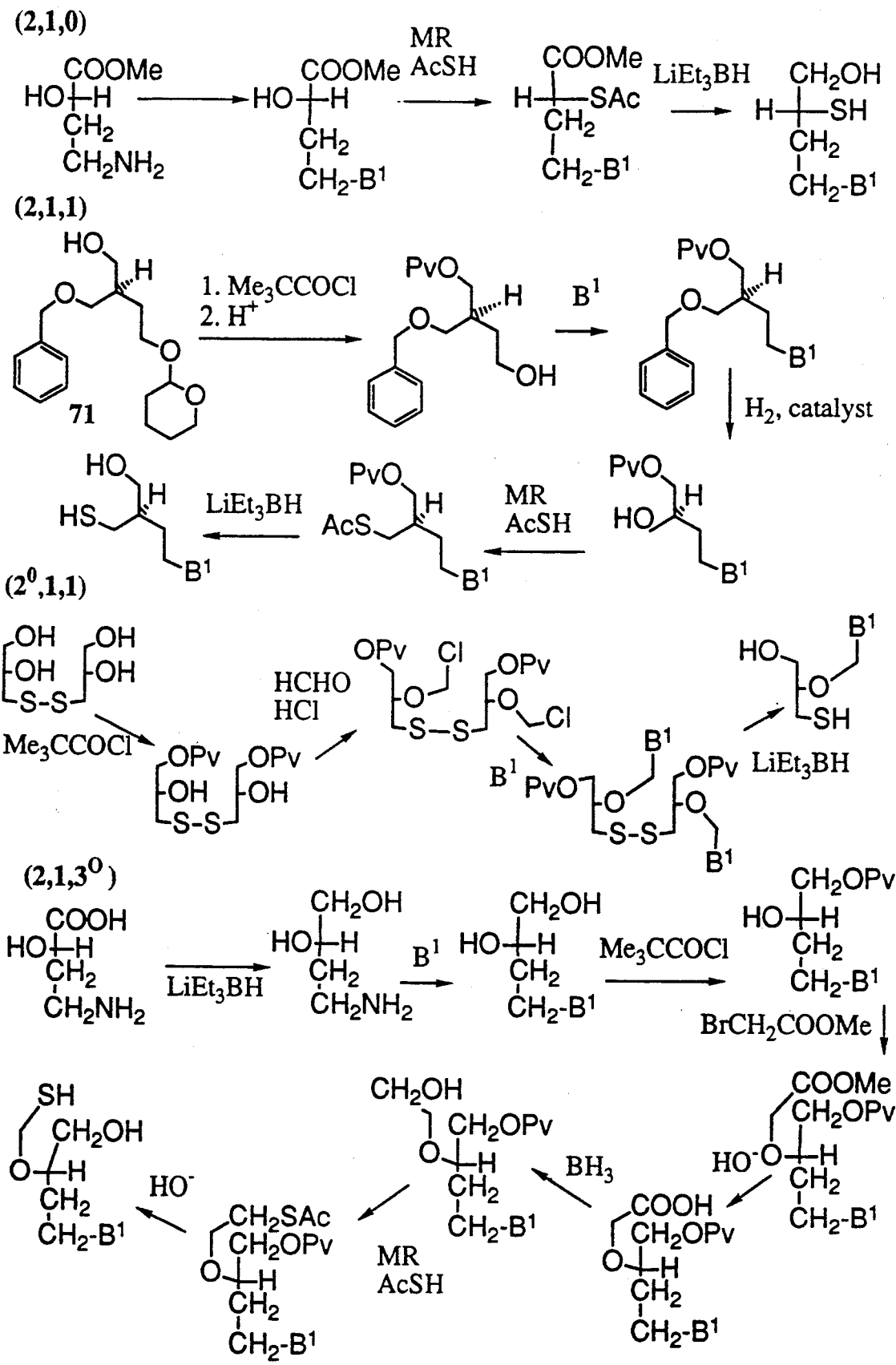
FIG. 16c depicts a synthetic route for preparing flexible nucleoside analog building blocks where the number of atoms joining the base analog to the backbone is 2.

Example 11 (FIG. 15)

Non-rigid, Not Isosteric, No Heteroatom in Linker, Classes (2,2,2) and (2,1,3)

1-R-Norbornanone 81

Pyridinium chlorochromate (23 g, 107 mmol) is stirred with Celite (22 g) and $CH_2Cl_2$ (140 ml) at RT. To the suspension is added (1S,2S)-norbornan-2-ol (80, 70 mmol; Brown, H. C.; Desai, M. C.; Jadhav, P. K. *J. org. Chem.*, 1982 47 5065–5069) in $CH_2Cl_2$ (70 ml) dropwise over a period of 30 min. The mixture is stirred for an hour at RT, at which point the dark brown suspension is filtered through silica gel (60 g). Chromatography yields (1R)-norbornanone 81.

This product is oxidized by the Baeyer-Villiger procedure. (1R)-Norbornanone (81, 18 mmol) is stirred with sodium acetate (9 g, water-free), hydrogen peroxide (27 ml, 30%), and acetic acid (9 ml) at 5° C. in the dark for 40 hours. The reaction is quenched by the addition of sodium sulfite (50 ml of a 10% aqueous solution) at 0° C. The product is extracted twice with EtOAc (600 ml). The extract is washed with the sodium sulfite solution, then with sodium bicarbonate solution (50 ml, saturated), then with sodium chloride solution (saturated), dried and evaporated. The product is chromatographed on silica (380 g, ether) to yield the lacton of 3 hydroxycyclopentane-1-acetic acid (82, 12 mmol, 67%).

This product is hydrolyzed in base, oxidized to 3-carboxymethylcyclopentanone (83) with chromic acid (vide supra), and oxidized again using a Baeyer-Villager procedure (vide supra) to yield a mixture of (4S)-2-oxa-4-carboxymethyl tetrahydropyran (84) and (5S)-2-oxa-5-carboxymethyl-tetrahydropyran (85). These compounds are separated, and serve as the skeletons for synthesis of flexible building blocks in Class (2,2,2) and (2,3,1), exemplified by structures 86 and 87, following the sequence of reactions shown in FIG. 15, using procedures analogous to those described in Examples 1–10.

What is claimed is:

1. A compound having a formula selected from the group consisting of

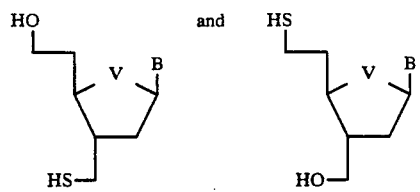

wherein

V is selected from the group consisting of —O— and —$CH_2$—;

B is a base analog that can form hydrogen bonds to natural oligonucleoside bases, wherein B is selected from the group consisting of adenine, 7-deazaadenine, 7-deaza-8-azaadenine, 3,7-dideazaadenine, 8-deazaadenine, guanine, 3-deazaguanine, 7-deaza-8-azaguanine, 3,7-dideazaaguanine, 3,7-dideaza-8-azaguanine, 7-deazaguanine, 8-azaguanine, purine, azapurine, 2,6-diaminopurine, hypoxanthine, uracil, 5-azauracil, 6-azauracil, 5-fluorouracil, 5-bromouracil, 5-iodouracil, thymine, 6-azathymine, cytosine, 6-azacytosine, 5-azacytosine, pyrimidine, azapyrimidine, pyrrolopyrimidine, pyrazolopyrimidine, triazolopyrimidine, imidazolopyrimidine, pyridine, imidazolopyridine, pyrrolopyridine, pyrazolopyridine and triazolopyridine.

2. A compound having the formula:

$$S_1(J_1-A_1-J_2-A_2)_nS_2$$

wherein n is an integer less than 25;

wherein $S_1$ is selected from the group consisting of alkyl and aralkyl and $S_2$ is selected from the group consisting of hydroxyl, S-alkyl and S-aralkyl;

$J_1$ and $J_2$ are linking groups independently selected from the group consisting of sulfide, sulfoxide, and sulfone whereby $J_1$ and $J_2$ may be different in each n subunit;

$A_1$ and $A_2$ may be different in each n subunit and are independently selected from the formulae consisting of:

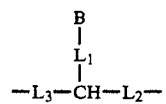
(II)

and

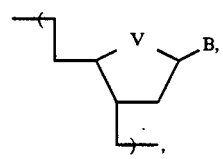
(III)

wherein V is independently selected from —O— or —$CH_2$—;

E is a base analog independently selected from the group consisting of adenine, 7-deazaadenine, 7-deaza-8-azaadenine, 3,7-dideazaadenine, 8-deazaadenine, guanine, 3-deazaguanine, 7-deaza-8-azaguanine, 3,7-dideazaaguanine, 3,7-dideaza-8-azaguanine, 7-deazaguanine, 8-azaguanine, purine, azapurine, 2,6-diaminopurine. hypoxanthine, uracil, 5-azauracil, 6-azauracil, 5-fluorouracil, 5-bromouracil, 5-iodouracil, thymine, 6-azathymine, cytosine, 6-azacytosine, 5-azacytosine, pyrimidine, azapyrimidine, pyrrolopyrimidine, pyrazolopyrimidine, triazolopyrimidine, imidazolopyrimidine, pyridine, imidazolopyridine, pyrrolopyridine, pyrazolopyridine and triazolopyridine;

$L_1$ is a linking roup containing from zero to four linking units independently selected from the group consisting of —CH$_2$—and —O—;

$L_2$ is a linking group containing from 1 to 5 linking units independently selected from the group consisting of —CH$_2$ and —O—;

$L_3$ is a linking group containing from 0 to 5 linking units independently selected from the group consisting of —CH$_2$— and —O—;

whereby for each $A_1$ or $A_2$ of formula (II), the number of linking units in $L_1$ is less than or equal to the sum of the number of linking units in $L_2$ and $L_3$.

3. A compound having the formula:

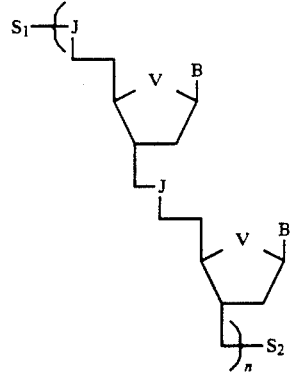

wherein
is an integer less than 25;
wherein $S_1$ is selected from the group consisting of alkyl and aralkyl and $S_2$ is selected from the group consisting of hyroxyl, 8-alkyl and 8-aralkyl,
J is a linking group independently selected from the group consisting of sulfide, sulfoxide, and sulfone,
V is independently selected from —O— or CH$_2$—; and
B is a base analog independently selected from the group consisting of adenine, 7-deazaadenine, 7-deaza-8-azaadenine, 3,7-dideazaadenine, 8-deazaadenine, guanine, 3-deazaguanine, 7-deaza-8-azaguanine, 3,7-dideazaaguanine, 3,7-dideaza-8-azaguanine, 7-deazaguanine, 8-azaguanine, purine, azapurine, 2,6-diaminopurine, hypoxanthine, uracil, 5-azauracil, 6-azauracil, 5-fluorouracil, 5-bromouracil, 5-iodouracil, thymine, 6-azathymine, cytosine, 6-azacytosine, 5-azacytosine, pyrimidine, azapyrimidine, pyrrolopyrimidine, pyrazolopyrimidine, triazolopyrimidine, imidazolopyrimidine, pyridine, imidazolopyridine, pyrrolopyridine, pyrazolopyridine and triazolopyridine,
whereby J, V, and B may be different in each n subunit.

* * * * *